(12) United States Patent
Kapadia et al.

(10) Patent No.: US 7,901,454 B2
(45) Date of Patent: Mar. 8, 2011

(54) APPARATUS AND METHOD FOR TREATING A REGURGITANT VALVE

(75) Inventors: Samir Kapadia, Orange, OH (US); Jay Yadav, Hunting Valley, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 87 days.

(21) Appl. No.: 11/638,864

(22) Filed: Dec. 14, 2006

(65) Prior Publication Data

US 2007/0198082 A1  Aug. 23, 2007

Related U.S. Application Data

(60) Provisional application No. 60/750,580, filed on Dec. 15, 2005.

(51) Int. Cl.
*A61F 2/24* (2006.01)
(52) U.S. Cl. .................. 623/2.11; 623/2.1; 623/2.2
(58) Field of Classification Search ....... 623/2.34–2.37, 623/2.11, 2.17; *A61F 02/24*
See application file for complete search history.

(56) References Cited

U.S. PATENT DOCUMENTS

| | | | |
|---|---|---|---|
| 4,727,873 A | 3/1988 | Mobin-Uddin | |
| 4,994,077 A | 2/1991 | Dobben | |
| 6,537,198 B1* | 3/2003 | Vidlund et al. ............. | 600/16 |
| 6,764,510 B2 | 7/2004 | Vidlund et al. | |
| 7,211,107 B2* | 5/2007 | Bruckheimer et al. ...... | 623/1.36 |
| 2002/0099433 A1* | 7/2002 | Fischell et al. ............. | 623/1.11 |
| 2004/0093060 A1 | 5/2004 | Seguin et al. | |
| 2004/0186566 A1* | 9/2004 | Hindrichs et al. .......... | 623/2.37 |
| 2004/0243229 A1* | 12/2004 | Vidlund et al. ............. | 623/2.34 |
| 2005/0021056 A1 | 1/2005 | St. Goar et al. | |
| 2005/0038508 A1 | 2/2005 | Gabbay | |
| 2005/0113910 A1 | 5/2005 | Paniagua et al. | |
| 2005/0137686 A1 | 6/2005 | Salahich et al. | |
| 2005/0267571 A1* | 12/2005 | Spence et al. .............. | 623/2.11 |
| 2006/0106279 A1* | 5/2006 | Machold et al. ............ | 600/37 |
| 2007/0093890 A1 | 4/2007 | Eliasen et al. | |
| 2008/0243245 A1* | 10/2008 | Thambar et al. ........... | 623/2.11 |

FOREIGN PATENT DOCUMENTS

WO  WO 2005/046530 A1  5/2005

* cited by examiner

*Primary Examiner* — Corrine M McDermott
*Assistant Examiner* — Jason-Dennis Stewart
(74) *Attorney, Agent, or Firm* — Tarolli, Sundheim, Covell & Tummino LLP

(57) ABSTRACT

An apparatus for treating regurgitation of blood through a diseased heart valve having at least two leaflets includes an occluding member configured to be positioned within the diseased heart valve so that at least a portion of the occluding member is positioned adjacent to one of the at least two leaflets. The at least one portion of the occluding member contacts at least one surface of the at least one leaflet. The occluding member is dimensioned so that the at least one leaflet abuts the at least one surface of the occluding member. The apparatus further includes a suspending wire operatively attached to the occluding member and configured to facilitate positioning of the occluding member within the heart valve. The suspending wire includes an anchoring portion having a coiled shape. The anchoring portion is configured to secure the suspending wire to at least one of a blood vessel and a heart wall surrounding a heart chamber.

10 Claims, 23 Drawing Sheets

APPARATUS AND METHOD FOR TREATING A REGURGITANT VALVE

RELATED APPLICATION

This application claims priority from U.S. Provisional Application No. 60/750,580, filed Dec. 15, 2005, the subject matter of which is incorporated here by reference.

TECHNICAL FIELD

The present invention relates to an apparatus and method for treating and improving the function of dysfunctional heart valves. More particularly, the present invention relates to an apparatus and method that passively assists in closing the native valve leaflets to improve valve function of a regurgitant heart valve.

BACKGROUND OF THE INVENTION

A heart valve may become defective or damaged from degeneration caused by congenital malformation, disease, aging, and the like. When the valve becomes defective or damaged, the leaflets may not function properly to effectively prevent blood flow through the valve when appropriate. For example, when a mitral valve functions properly, the mitral valve prevents regurgitation of blood from the left ventricle into the left atrium when the ventricle contracts. In order to withstand the substantial backpressure and prevent regurgitation of blood into the left atrium during the ventricular contraction, the chordae tendinae hold the anterior and posterior leaflets in place across the opening of the annular ring.

If the annulus of the mitral valve enlarges or dilates to a point where the attached leaflets are unable to fully close the opening (e.g, malcoaptation), regurgitation may occur. Further, valve prolapse, or the forcing of the valve annulus and leaflets into the left atrium by backpressure in the left ventricle, may occur. Adverse clinical symptoms, such as chest pain, cardiac arrhythmias, dyspnea, and the like may manifest in response to regurgitation or valve prolapse. As a result, surgical correction, either by valve repair procedures or by valve replacement, may be required.

Surgical reconstruction or repair procedures may include plication, chordal shortening, or chordal replacement. Another common repair procedure entails remodeling the valve annulus (e.g., annuloplasty) by implantation of a prosthetic ring to help stabilize the annulus and to correct or help prevent valve insufficiency. In situations where the valve leaflets exhibit lesions, reconstruction of one or more valve leaflets by securing grafts or patches to the leaflets, such as over lesions or holes formed in the leaflets, may be necessary. The repair or reconstruction of the leaflets can be complicated and time consuming.

SUMMARY OF THE INVENTION

In one aspect of the present invention, an apparatus for treating regurgitation of blood through a diseased heart valve having at least two leaflets comprises an occluding member configured to be positioned within the diseased heart valve so that at least a portion of the occluding member is positioned adjacent to one of the at least two leaflets of the heart valve. The at least one portion of the occluding member contacts at least one surface of the at least one leaflet. The occluding member is dimensioned so that, during at least a portion of the cardiac cycle, the at least one leaflet abuts the at least one surface of the occluding member to mitigate regurgitation of blood through the heart valve. The apparatus further includes a suspending wire operatively attached to the occluding member and configured to facilitate positioning of the occluding member within the heart valve. The suspending wire includes an anchoring portion having a coiled shape. The anchoring portion is configured to secure the suspending wire to at least one of a blood vessel and a heart wall surrounding a heart chamber containing the heart valve.

In another aspect of the present invention, a method is provided for treating regurgitation of blood through a diseased heart valve. One step of the method provides an apparatus comprising an occluding member operatively attached to a suspending wire having an anchoring portion. Next, a balloon is positioned in the diseased heart valve to determine the size and shape of the diseased heart valve. An occluding member having a size and shape that corresponds to the size and shape of the diseased heart valve is then selected so that at least one leaflet of the heart valve coapts with the occluding member. The apparatus is next introduced into a patient's body and subsequently positioned in one chamber of the patient's heart.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
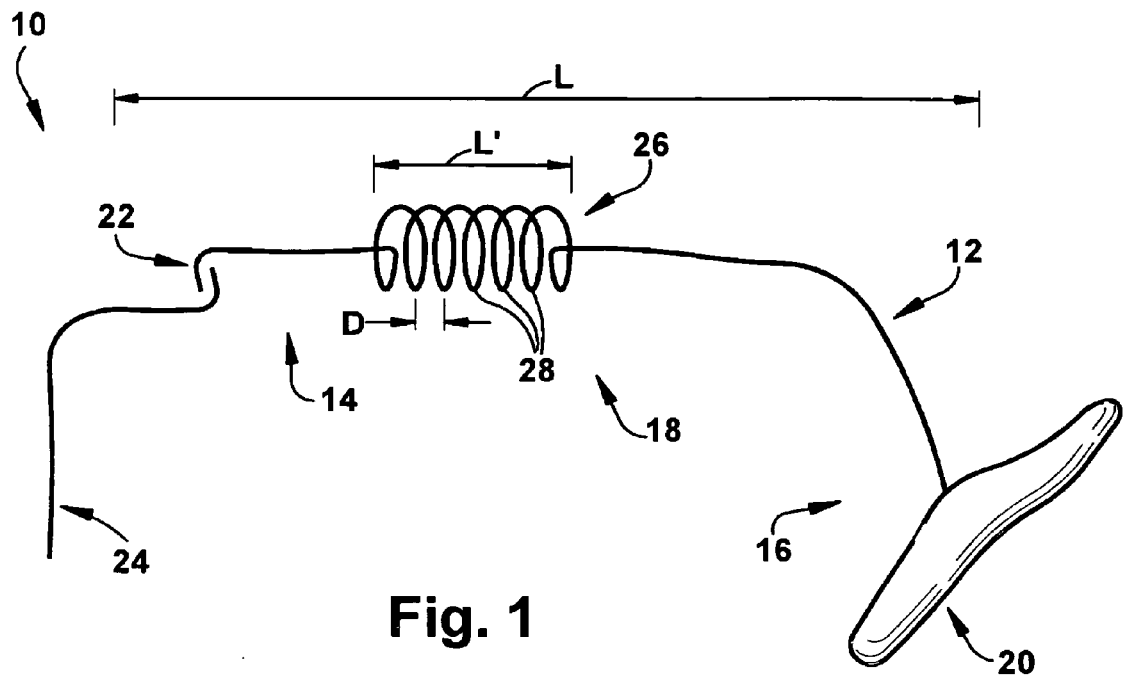
FIG. 1 is a side view of an apparatus for treating a regurgitant heart valve in accordance with the present invention.

The present invention relates to an apparatus and method for treating and improving the function of dysfunctional heart valves. More particularly, the present invention relates to an apparatus and method that passively assists in closing the native leaflets to improve valve function of a regurgitant valve. As representative of the present invention, FIG. 1 illustrates an apparatus 10 for treating regurgitation of blood through a diseased heart valve 30 (FIG. 2) having at least two leaflets.

Figure 2:
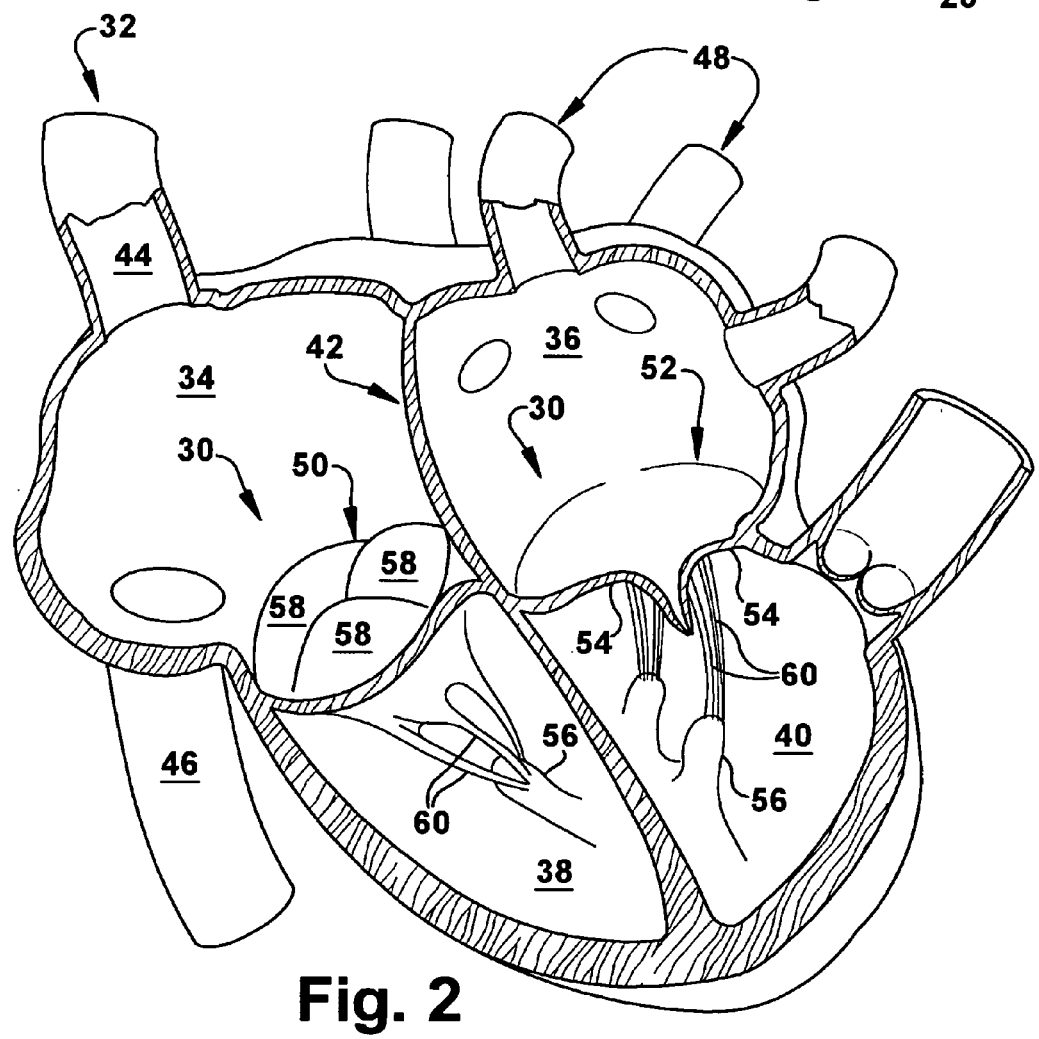
FIG. 2 is a cross-sectional schematic view of a human heart.

FIG. 2 schematically illustrates a human heart 32 which includes four chambers: the right and left atria 34 and 36, respectively, and the right and left ventricles 38 and 40, respectively. The right and left atria 34 and 36 are divided by the interatrial septum 42. The thin-walled right atrium 34 receives deoxygenated blood from the superior vena cava 44, the inferior vena cava 46, and from the coronary sinus 68 (FIG. 3B). The thin-walled left atrium 36 (FIG. 2) receives oxygenated blood from pulmonary veins 48. The right and left ventricles 38 and 40 pump oxygenated and deoxygenated blood, respectively, throughout the body, and the pocket-like semilunar pulmonary valve 49 (FIG. 3A) and the aortic valve 66 prevent reflux into the ventricles. Atrial blood is pumped through the atrioventricular orifices, guarded by the tri-leaflet tricuspid valve 50 (FIG. 2) on the right side of the heart 32 and the bi-leaflet mitral valve 52 on the left side of the heart. The free edges of the leaflets 54 of the mitral valve 52 are attached to the papillary muscles 56 in the left and right ventricles 40 and 42 by chordae tendineae 60. Similarly, the free edges of the leaflets 58 of the tricuspid valve 50 are attached to the papillary muscles 56 in the left and right ventricles 40 and 42 by chordae tendineae 60.

Figure 3A:
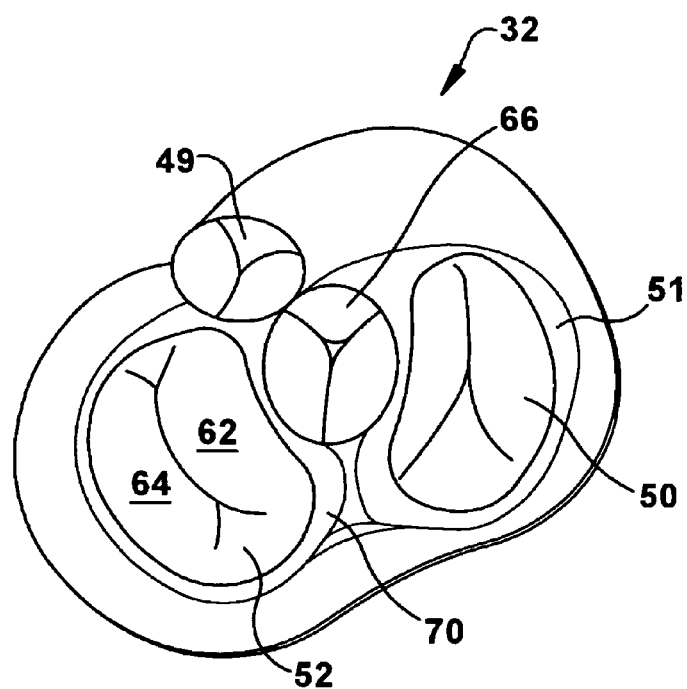
FIG. 3A is a short-axis cross-sectional view of the human heart.
Figure 3B:
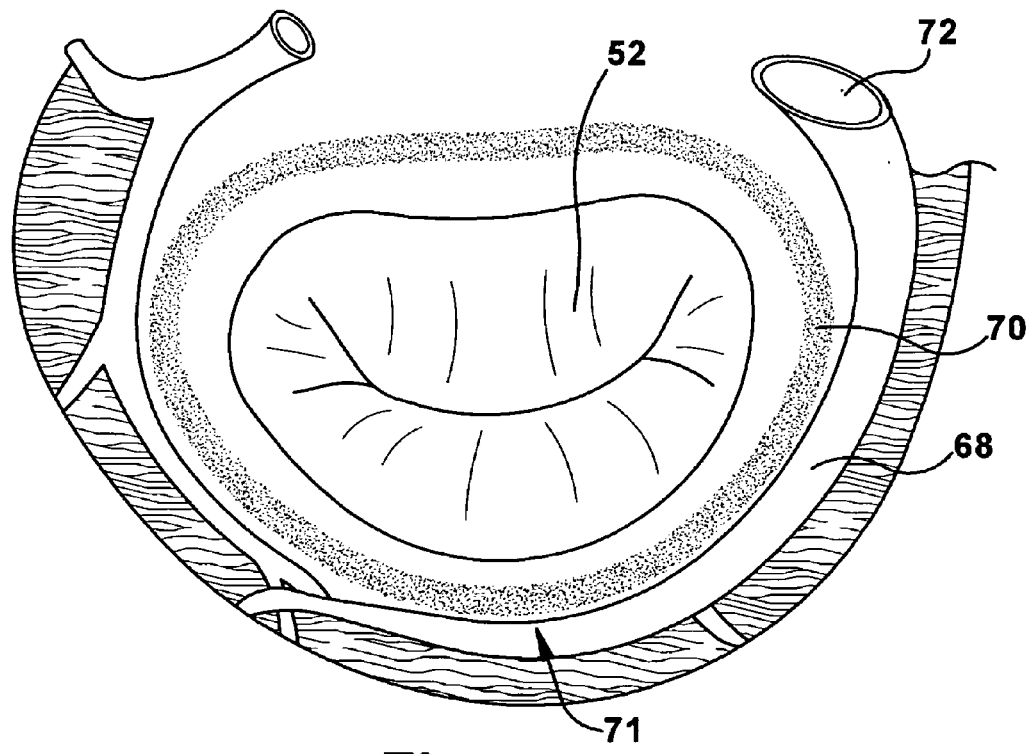
FIG. 3B is a partial short-axis cross-sectional view of the human heart.

FIG. 3A is a short-axis cross-sectional view of the heart 32 illustrating the mitral valve 52 in relation to the other valves of the heart; namely, the aortic valve 66, the tricuspid valve 50, and the pulmonary valve 49. The mitral valve 52 has two leaflets; an anterior leaflet 62 and a posterior leaflet 64. The anterior leaflet 62 is adjacent the aorta (not shown), and the posterior leaflet 64 is opposite the aorta. FIG. 3B is a partial short-axis cross-sectional view showing the mitral valve 50 in relation to the coronary sinus 68. The coronary sinus 68 wraps around a significant portion of the posterior aspect 71 of the mitral valve annulus 70. The ostium 72 of the coronary sinus 68 drains into the right atrium 34.

Figure 4A:
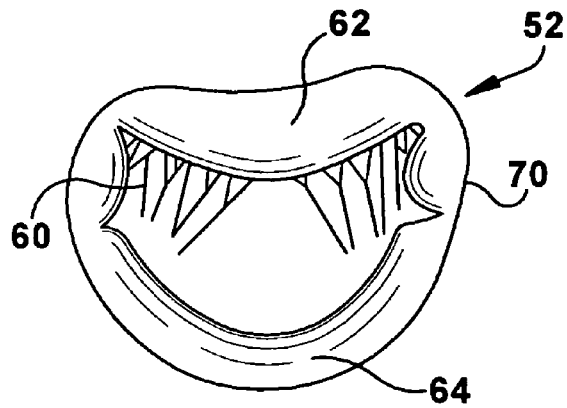
FIG. 4A is a top view of a properly functioning mitral valve in an open position.
Figure 4B:
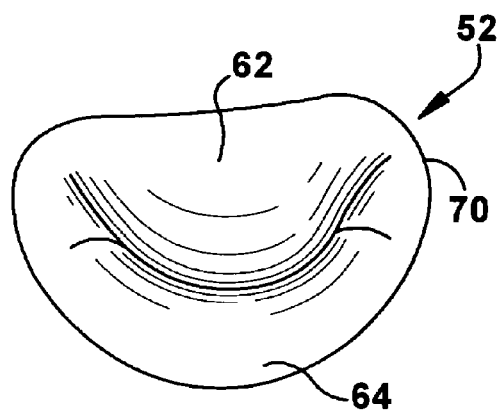
FIG. 4B is a top view of a properly functioning mitral valve in a closed position.

In FIGS. 4A and 4B, a top view of a properly functioning mitral valve 52 is shown. FIG. 4A shows the mitral valve 52 in its open position during diastole in which the posterior leaflet 64 is separated from the anterior leaflet 62. Portions of the chordae tendinae 60 can also be seen in FIG. 4A. FIG. 4B shows the properly functioning mitral valve 52 in the closed position during systole. In this figure, the anterior leaflet 62 and the posterior leaflet 64 contact one another and close the mitral valve 52 to prevent blood from flowing through the mitral valve from the left atrium 36 to the left ventricle 40.

Figure 4C:
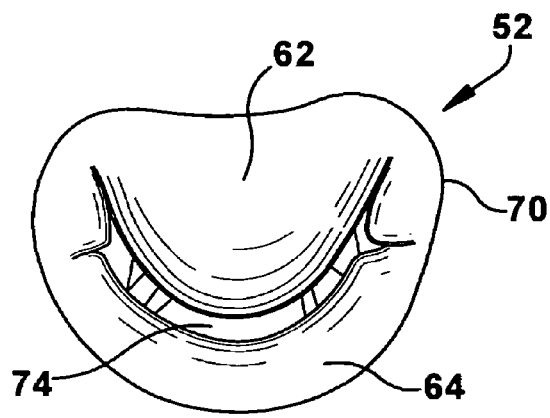
FIG. 4C is a top view of an improperly functioning mitral valve in a closed position.

FIG. 4C shows a top view of an improperly functioning mitral valve 52 in the "closed" position (i.e., during systole). In FIG. 4C, a regurgitant mitral valve orifice 74 is formed when the anterior leaflet 62 and the posterior leaflet 64 do not properly coapt. This may be caused by, for example, a dilatation of the annulus 70 caused by an enlargement of the left ventricle 40. As shown in FIG. 4C, this improper coaptation prevents the complete closure of the orifice 74 between the valve leaflets 62 and 64, thereby permitting blood to leak through the valve 52 from the left ventricle 40 to the left atrium 36 during systole. In other words, although the mitral valve 52 is in a contracted state, it is not actually closed so as to prevent blood flow therethrough since the leaflets 62 and 64 do not completely come together.

Figure 5A:
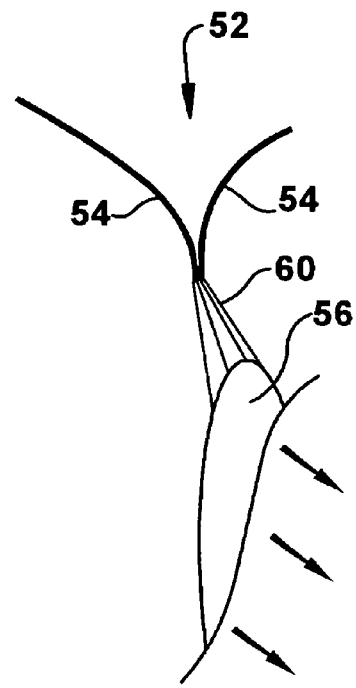
FIG. 5A is a side view of a properly functioning mitral valve shown with its connection to the papillary muscles.
Figure 5B:
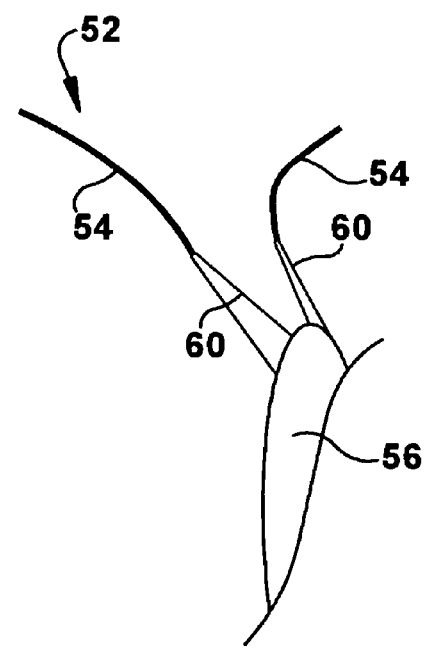
FIG. 5B is a side view of an improperly functioning mitral valve shown with its connection to the papillary muscles.

FIG. 5A shows a side view of a properly functioning mitral valve 52 in the closed position with the valve leaflets 62 and 64 properly coapted so as to prevent blood flow through the valve. The arrows in FIG. 5A show the movement of the papillary muscles 56 down and to the right resulting from such ventricle dilatation. FIG. 5B shows a side view of an improperly functioning mitral valve 52 in which the valve leaflets 62 and 64 are not properly coapted due to, for example, dislocation of the papillary muscles 56. Such dislocation of the papillary muscles 56 may also be caused by enlargement of the left ventricle 40.

Such dysfunctional valves 52, as shown in FIGS. 4C and 5B, may cause a reduction in forward stroke volume from the left ventricle 40. Also, a blood flow reversal into the pulmonary veins 48 may occur. Regurgitation of the mitral valve 52 may also arise from a combination of a dilated valve annulus 70 and papillary muscle 56 dislocation.

As illustrated in FIG. 1, the apparatus 10 of the present invention comprises a suspending wire 12 having proximal and distal end portions 14 and 16. The suspending wire 12 has a wire-like configuration and may have a rigid, semi-rigid, or flexible shape. The suspending wire 12 may be constructed of either monofilament or multifilament constructions, such as braids or cables, for example. The suspending wire 12 may be made from a biocompatible material or may otherwise be treated with a material or combination of materials to impart biocompatability. Materials such as high strength polymers, including liquid crystal polymers and ultra high molecular weight polyethylene fibers may be suitable to provide desirable mechanical and fatigue properties. Suitable metals may include stainless steel, titanium alloys, and cobalt-chrome alloys, for example.

The distal end portion 16 of the suspending wire 12 further comprises an occluding member 20 which assists in closing the mitral valve 52 to prevent regurgitation by increasing the coaptation area of the mitral valve leaflets 54 and/or decreasing the coaptation depth of the mitral valve leaflets. Increasing coaptation of the mitral valve 52 is generally accomplished by placing the occluding member 20 in the regurgitant mitral valve orifice 74, thereby providing a surface against which the mitral valve leaflets 54 may abut (i.e., coapt) in order to close the mitral valve during systole. The occluding member 20 assists in substantially closing the mitral valve 52 without altering the shape of the valve annulus 70 and/or repositioning the papillary muscles 56.

Figure 6A:
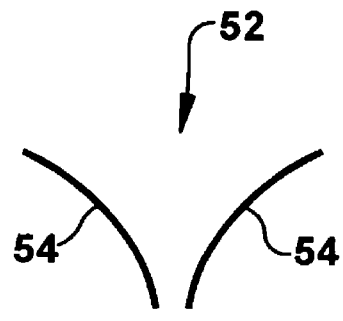
FIG. 6A is a schematic side view of an improperly functioning mitral valve during systole.
Figure 6B:
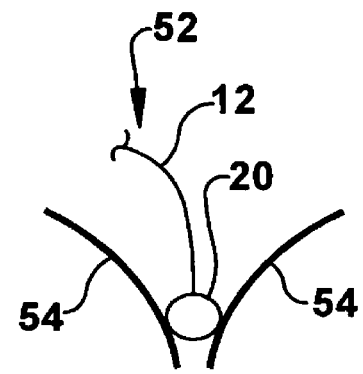
FIG. 6B is a schematic side view of the valve of FIG. 6A with an occluding member implanted in the valve orifice.

FIG. 6A illustrates a schematic side view of the leaflets 54 of a dysfunctional mitral valve 52 during systole. As seen in FIG. 6A, the leaflets 54 do not coapt so as to close the regurgitant mitral valve orifice 74. Therefore, regurgitant flow will occur through the valve 52 during systole. FIG. 6B illustrates the valve 52 of FIG. 6A during systole with the occluding member 20 implanted in the regurgitant mitral valve orifice 74. As can be seen, the presence of the occluding member 20 will block regurgitant blood flow through the valve 52 during systole as the leaflets 54 abut against the surface of the occluding member. In other words, the occluding member 20 "plugs" the regurgitant mitral valve orifice 74 during systole to hinder or prevent blood from leaking through the valve 52.

In FIGS. 7A-7G, the occluding member 20 is suspended in the regurgitant mitral valve orifice 74. The suspended occluding member 20 may have a variety of shapes depending on factors such as the geometry of the mitral valve 52, the alignment of the valve leaflets 54, and the size and shape of the regurgitant mitral valve orifice 74 during systole. For example, the occluding member 20 may have a solid, semi-solid, or mesh-like configuration. As described in further detail below, the occluding member 20 may be partly or completely covered by a membrane (not shown), the composition of which may be organic, inorganic, or a combination thereof.

Figure 7A:
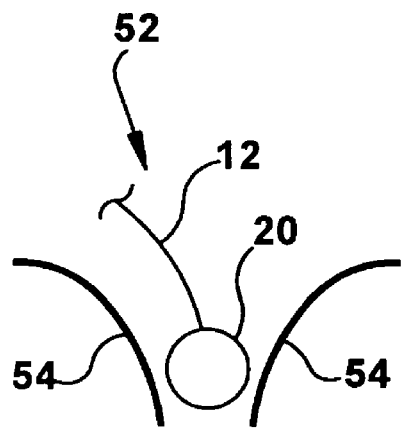
FIG. 7A is an exemplary embodiment of a spherical occluding member implanted in the mitral valve orifice between the valve leaflets.
Figure 7B:
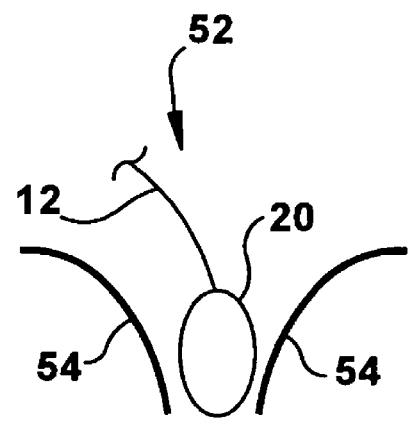
FIG. 7B is an exemplary embodiment of an ellipsoidal occluding member implanted in the mitral valve orifice between the valve leaflets.
Figure 7C:
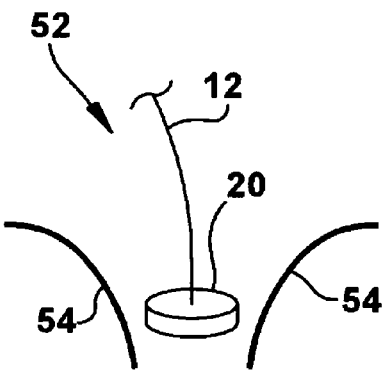
FIG. 7C is an exemplary embodiment of a disk-shaped occluding member implanted in the mitral valve orifice between the valve leaflets.
Figure 7D:
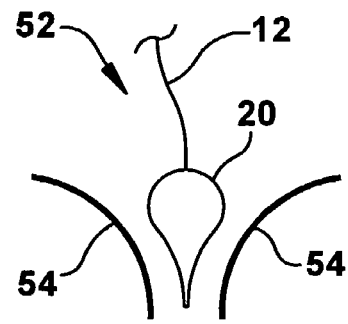
FIG. 7D is an exemplary embodiment of a wing-shaped occluding member implanted in the mitral valve orifice between the valve leaflets.
Figure 7E:
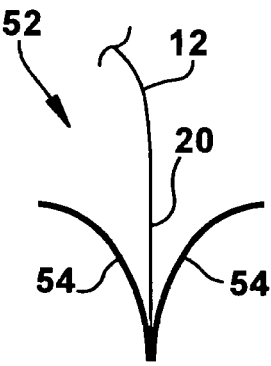
FIG. 7E is an exemplary embodiment of a sheet-like occluding member implanted in the mitral valve orifice between the valve leaflets.

As illustrated in FIGS. 7A-7G, the occluding member 20 may have a variety of shapes and configurations. For instance, the occluding member 20 may have a spherical configuration (FIG. 7A), an ellipsoidal configuration (FIG. 7B), a disk-shaped configuration (FIG. 7C), a wing-like configuration (FIG. 7D), or a sheet-like configuration (FIG. 7E). The occluding member 20 may additionally have a valvular configuration (not shown). Where the occluding member 20 has a valvular configuration, the occluding member may comprise a prosthetic heart valve, such as a mechanical or bioprosthetic heart valve.

Mechanical heart valves are made from materials of synthetic origin like metals (e.g., stainless steel and molybdenum alloys), ceramics and polymers. Mechanical heart valves typically utilize a ball, a disc, valve leaflets or other mechanical valving devices to regulate the direction of blood flow through the prosthesis. Specific examples of mechanical heart valves are known in the art. In addition to synthetic materials, materials of biological origin (e.g., bovine pericardial tissue, equine pericardial tissue, or bovine pericardial tissue) are typically used to construct bioprosthetic heart valves. Specific examples of bioprosthetic heart valves are known in the art.

Figure 7F:
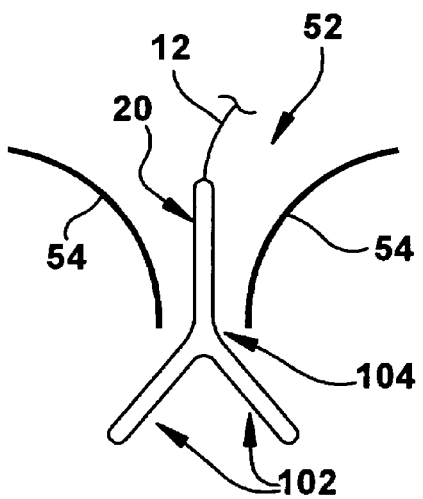
FIG. 7F is an exemplary embodiment of a Y-shaped occluding member implanted in the mitral valve orifice between the valve leaflets during diastole.
Figure 7G:
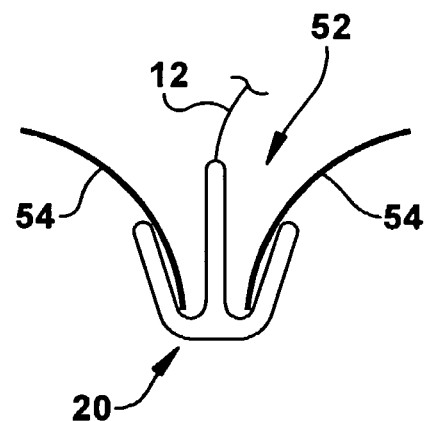
FIG. 7G is an exemplary embodiment of an umbrella-shaped occluding member implanted in the mitral valve orifice between the valve leaflets during systole.

Additionally, the occluding member 20 may have a Y- or umbrella-shaped configuration, depending upon the cardiac cycle (i.e., diastole or systole). As shown in FIGS. 7F and 7G, the occluding member 20 may include flexible wing members 102 operatively connected at a junction 104. As illustrated in FIG. 7F, diastolic blood flow causes the occluding member 20 to obtain a Y-shaped configuration, consequently permitting blood flow from the left atrium 36 into the left ventricle 40. Then, during systole, the occluding member 20 obtains an umbrella-like configuration so that the flexible wing members 102 coapt with the valve leaflets 54 as shown in FIG. 7G and regurgitant blood flow through the valve 52 is substantially reduced or eliminated.

The occluding member 20 may also include an actuatable mechanism (not shown) which may serve to vary the size of the occluding member during systole and diastole. The actuatable mechanism may comprise, for example, a pressure-sensitive switch (not shown) capable of causing the occluding member 20 to obtain a collapsible configuration during diastole and a collapsed configuration during systole. Thus, during diastole, the occluding member 20 would have an expanded configuration so that blood can flow between the leaflets 54 and the surface of the occluding member. Then, during systole, the collapsible configuration would allow the leaflets 54 to close against the occluding member 20 so that blood is substantially prevented from flowing through the mitral valve 52.

The particular position selected to implant the occluding member 20 may depend on a variety of factors, such as the condition of the patient's heart 32, including the valve leaflets 54, the delivery technique utilized to implant the apparatus 10, the type of occluding member utilized to treat the valve 52, and other similar factors. Each of the positions shown in FIGS. 7A-7F, however, permits proper positioning of the occluding member 20 to prevent regurgitation and avoid damage to key coronary structure. Further, particular positions may be selected based on factors such as the geometry, including size and shape, of the regurgitant mitral valve orifice 74. For instance, the occluding member 20 may be configured to be positioned between the valve leaflets 54, below the free ends of the valve leaflets, or at a level of the valve annulus 70 so that the occluding member permits the valve 52 to close during systole and thus prevent regurgitant blood flow from occurring.

As noted above, materials suitable for construction of the occluding member 20 may be organic, inorganic, or a combination thereof. Suitable materials may be categorized generally into the following broad groups: synthetic polymers, biological polymers, metals, ceramics and biological materials. Suitable synthetic polymers may include fluoroethylenes, silicones, urethanes, polyamides, polyimides, polysulfone, polyether ketones, polymethyl methacrylates, and the like.

Suitable metals may be composed from a variety of biocompatible elements or alloys. Examples include titanium, Ti-6AL-4V, stainless steel alloys, chromium alloys, and cobalt alloys. The stainless steel alloys may include, for example, 304 and 316 stainless steel alloys. The cobalt alloys may include Elgiloy, MP35N, and Stellite, for example.

Suitable ceramic materials may be fashioned from pyrolytic carbon and other diamond-like materials, such as zirconium, for example. These materials may be applied to a variety of core materials, such as graphite, for example.

As for biological materials for use with the occluding member 20, a variety of fixed tissues may be used, including, for example, pericardium, peritoneum, facia mater, dura mater, and vascular tissues. Tissues may be fixed with a variety of chemical additives, such as aldehydes and epoxies, for example, so as to render them non-immunogenic and biologically stable. Engineered tissues may also be used with the occluding member 20. Tissue substrates may be constructed from a variety of materials, such as resorbable polymers (e.g., polylactic acid, polyglycolic acid, or collagen). These substrates may then be coated with biologically active molecules to encourage cellular colonization. Additionally, these tissues may be constructed in vitro, for example using the patient's own cells or using universal cell lines. In this way, the tissue may maintain an ability to repair itself or grow with the patient. This may be particularly advantageous in the case of pediatric patients, for example.

The biological materials may also be subjected to surface modification techniques to make them selectively bioreactive or non-reactive. Such modification may include physical modification, such as texturing; surface coatings, including hydrophilic polymers and ceramics (e.g., pyrolytic carbon, zirconium nitrate, and aluminum oxide); electrical modification, such as ionic modification; or coating or impregnation of biologically derived coatings, such as heparin, albumin, and a variety of growth healing modification factors (e.g., vascular endothelial growth factors or cytokines).

Referring again to FIG. 1, the proximal end portion 14 of the suspending wire 12 includes a connecting mechanism 22 (not shown in detail) for connecting the suspending wire to a positioning wire 24. The positioning wire 24 can include, for example, a wire catheter. The connecting mechanism 22 may include a variety of devices or mechanisms capable of operably interlocking the suspending wire 12 with the positioning wire 24 and, when desired, disconnecting the suspending wire from the positioning wire. Examples of devices or mechanisms capable of operably interlocking the suspending wire 12 and the positioning wire 24 include magnetic locks, lock-and-key-styled devices, and the like.

The distance between the proximal and distal end portions 14 and 16 of the apparatus 10 define a first length L and comprise an intermediate portion 18. As shown in FIG. 1, the intermediate portion 18 further comprises an anchoring portion 26 capable of securing the suspending wire 12 to a heart wall surrounding the left ventricle 40. The anchoring portion 26 has a spiral or coiled shape and is defined by a second length L'. The anchoring portion 26 comprises a plurality of loop members 28, each of which is substantially parallel to one another and spaced apart by a distance D. The size of the loop members 28, the distance D between loop members, and the overall second length L' may vary depending upon clinical need. For example, the distance D between loop members 28 may be increased or decreased depending upon the thickness of the heart wall surrounding the left ventricle 40. Additionally, by varying the number and size of loop members 28, the flexibility of the suspending wire 12 may be varied.

Figure 8:
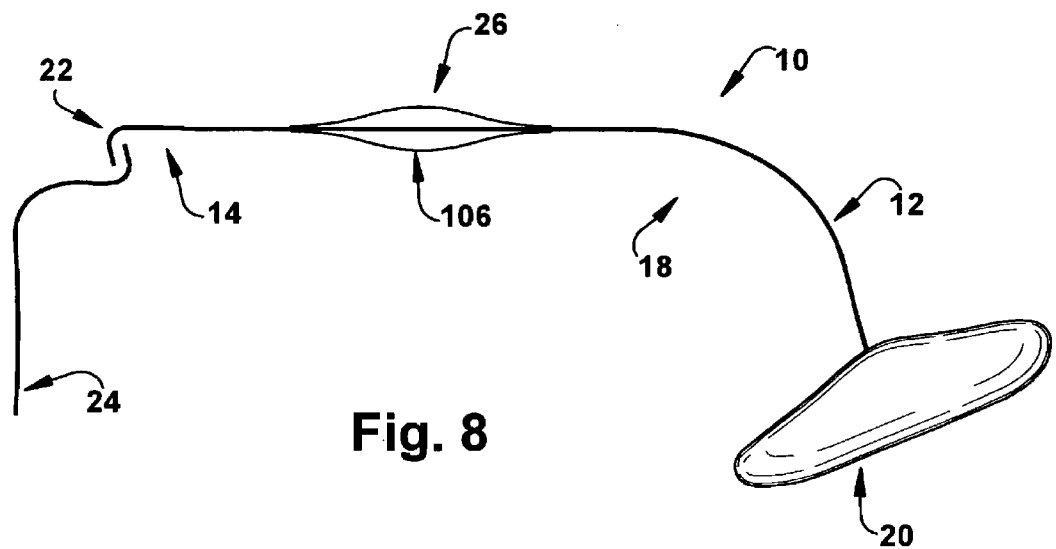
FIG. 8 is an alternative embodiment of the anchoring portion of the apparatus shown in FIG. 1 in a collapsed configuration.
Figure 8A:
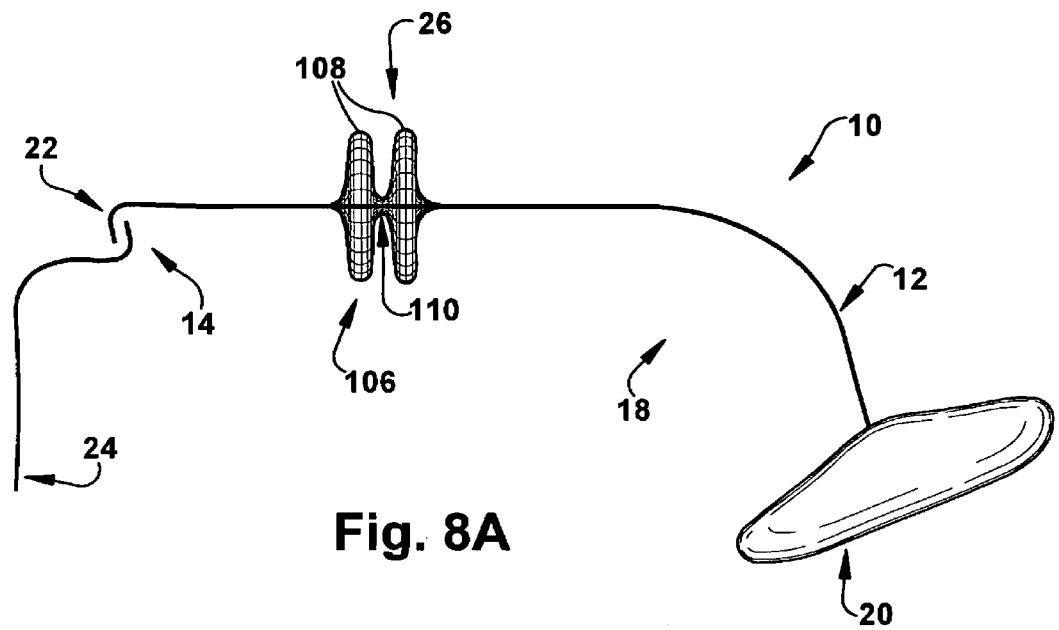
FIG. 8A is an expanded configuration of the anchoring portion shown in FIG. 8.

As shown in FIGS. 8 and 8A, the anchoring portion 26 may alternatively comprise a septal occluder 106. Various types of septal occluders are known in the art. For instance, the AMPLATZER® septal occluder, available from AGA Medical Corporation, located in Golden Valley, Minn., is a self-expandable, double disc device made from Nitinol wire mesh. The two discs are linked together by a short connecting waist corresponding to the size of the interatrial septum. In order to increase the closing ability of the AMPLATZER® septal occluder, the discs and the waist are filled with polyester fabric.

The septal occluder 106 of the present invention may be configured in a manner similar to the AMPLATZER® septal occluder. The septal occluder 106 may be self-expandable and may be comprised of a flexible material such as Nitinol. The septal occluder 106 may have two configurations; a collapsed configuration (FIG. 8) and an expanded configuration (FIG. 8A). In the expanded configuration, the septal occluder 106 may include a plurality of oppositely opposed flexible discs 108 which are fluidly connected by a connecting waist 110 intermediate the flexible discs. The flexible discs 108 and the connecting waist 110 may be appropriately- sized so that the septal occluder 106, in its expanded configuration, is securely positioned about the interatrial septum 42 to prevent or hinder unwanted movement or flexion of the apparatus 10.

Figure 8B:
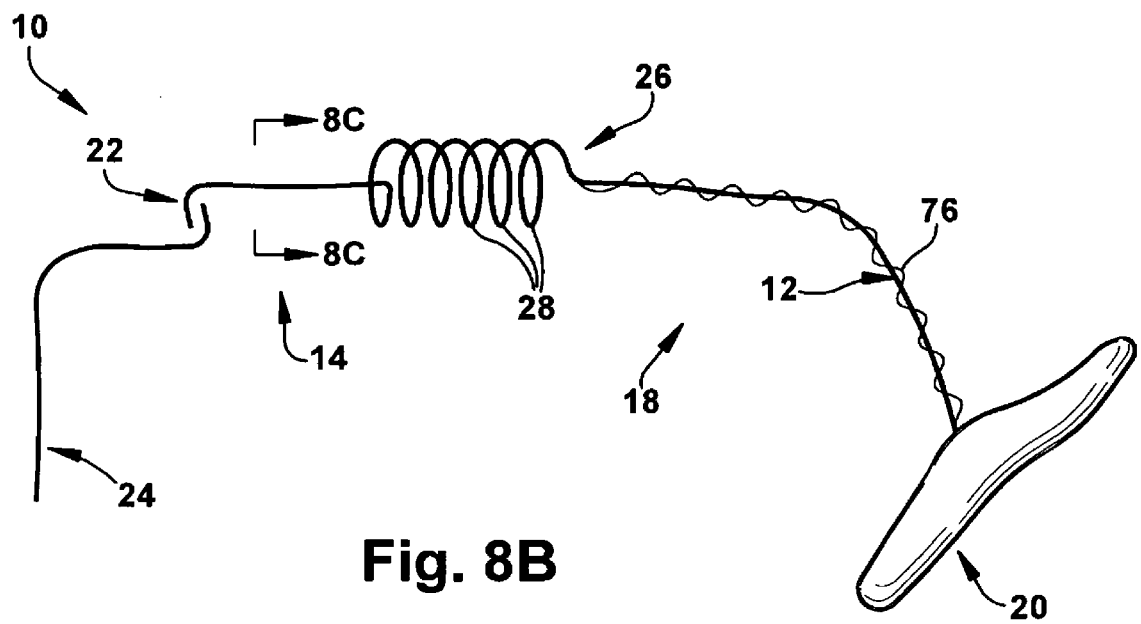
FIG. 8B is an alternative embodiment of the apparatus shown in FIG. 1.
Figure 8C:
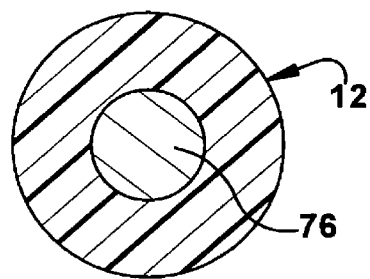
FIG. 8C is another alternative embodiment of the apparatus shown in FIG. 1.

Alternative embodiments of the present invention are shown in FIGS. 8B and 8C. In case the suspending wire 12 is fractured or broken, a safety wire 76 will temporarily hold the occluding member 20 so that the occluding member does not detach and become a loose object. As illustrated in FIG. 8B, the safety wire 76 may extend between the proximal and distal end portions 14 and 16 of the apparatus 10. As shown in FIG. 8B, the safety wire 76 may be positioned along the suspending wire 12 and independently attached thereto at a plurality of points.

The safety wire 76 may be wrapped or coiled around the suspending wire 12 so that the safety wire is operatively secured to the suspending wire. The safety wire 76 may also be connected between the anchoring portion 26 and occluding member 20 so that the safety wire thereby extends in a substantially parallel manner along the suspending wire 12. The safety wire 76 may be connected to the apparatus 10 using sutures, adhesives, clips, pins, or other similar means.

As shown in FIG. 8C, the safety wire 76 could alternatively lie coaxially within the suspending wire 12. The safety wire 76 may be sufficiently flexible so as to not be subjected to the stress and strain of the suspending wire 12. Materials used to construct the safety wire 76 may be biocompatible and/or coated, impregnated, or otherwise treated with a material or other materials to impart biocompatability. Materials suitable for construction of the safety wire 76 include, for example, Nitinol and Nitinol alloys, stainless steel and stainless steel alloys, titanium and titanium alloys, cobalt-chrome alloys, and the like. The safety wire 76 may alternatively comprise a thread or combination of threads made of, for example, nylon, braided nylon, polytetrafluoroethylene (PTFE), expanded PTFE (ePTFE), medical-grade sutures, and the like.

Figure 9A:
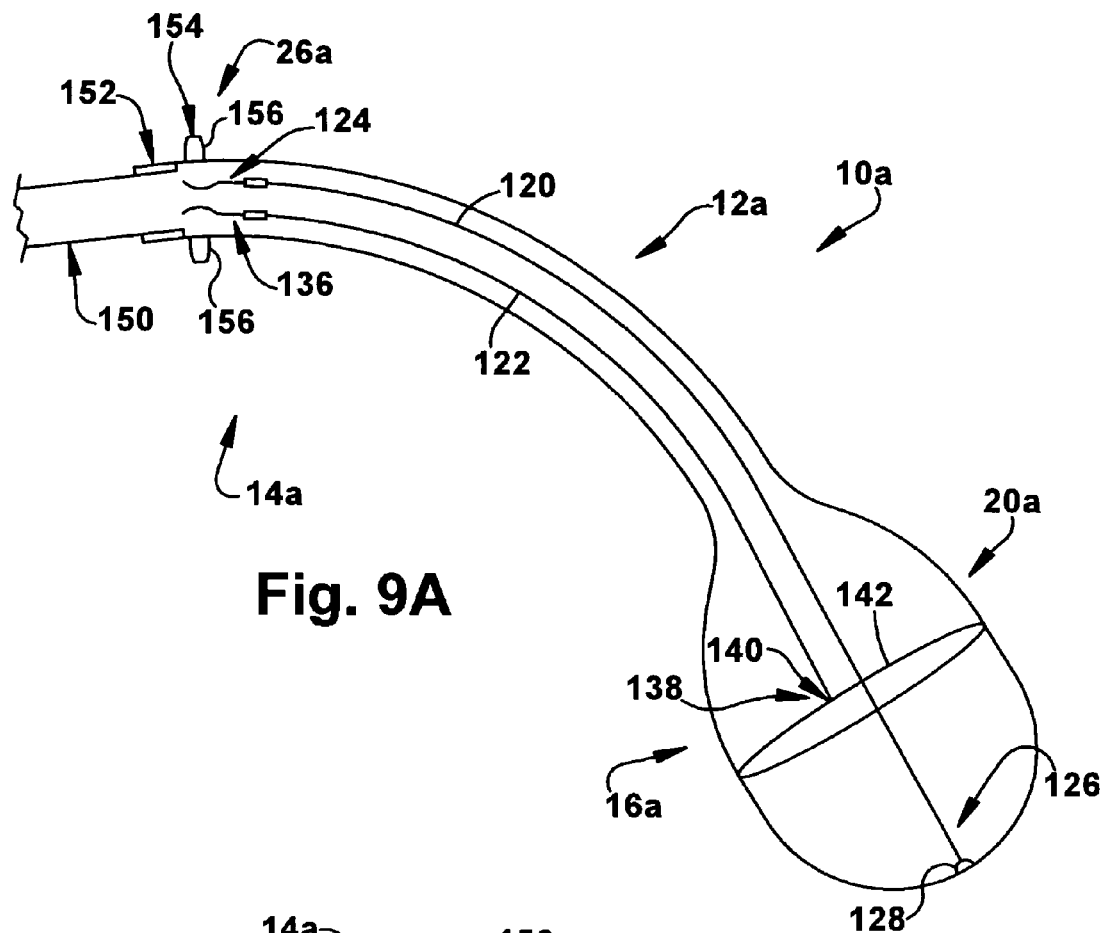
FIG. 9A is another alternative embodiment of the apparatus shown in FIG. 1.
Figure 9B:
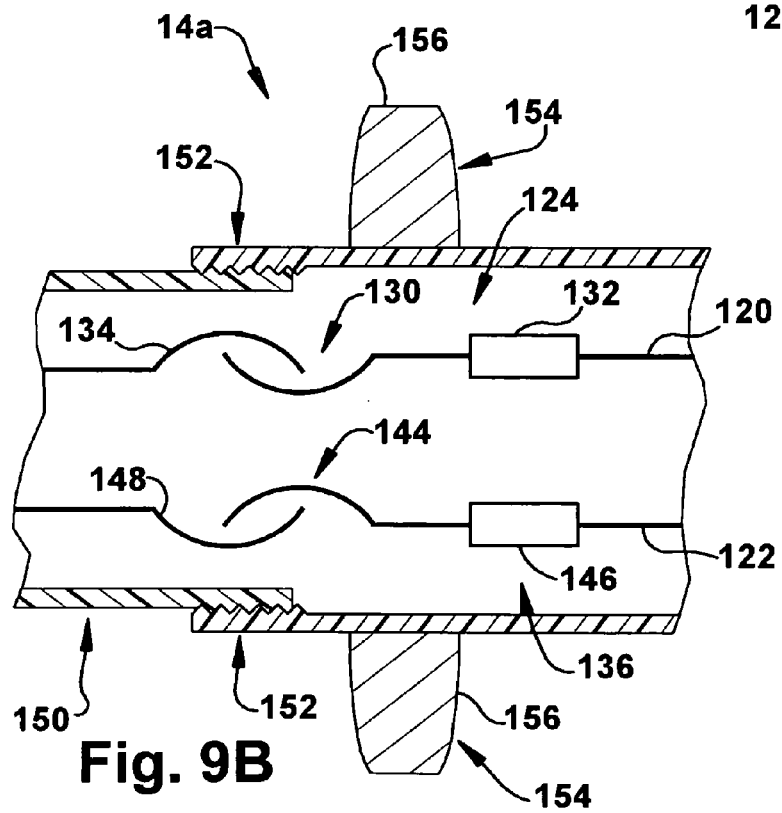
FIG. 9B is an exploded view showing the proximal end portion of the apparatus in FIG. 9A.

Another embodiment of the present invention is illustrated in FIGS. 9A and 9B. The apparatus 10a shown in FIGS. 9A and 9B is identically constructed as the apparatus shown in FIG. 1, except as described below. In FIGS. 9A and 9B, structures that are identical as structures in FIG. 1 use the same reference numbers, whereas structures that are similar but not identical carry the suffix "a".

As shown in FIG. 9A, the apparatus 10a may comprise a suspending wire 12a having proximal and distal end portions 14a and 16a. The proximal and distal end portions 14a and 16a may respectively comprise an anchoring portion 26a and an occluding member 20a. The suspending wire 12a may be made of a yieldable, flexibly resilient material such as wire-mesh, PTFE, ePTFE, or the like. The suspending wire 12a may further comprise first and second control wires 120 and 122 extending between the proximal and distal end portions 14a and 16a of the apparatus 10a as shown in FIG. 9A.

The first control wire 120 may comprise a proximal end portion 124 and a distal end portion 126. The distal end portion 126 may be operatively connected to the occluding member 20a at a first connecting point 128. The proximal end portion 124 may include a first attachment mechanism 130 (FIG. 9B) operatively connected to a first tensioning mechanism 132 (FIG. 9B). The first tensioning mechanism 132 may include a screw, for example, and may be manipulated so as to selectively adjust or fine-tune the vertical tension of the occluding member 20a. For example, the vertical tension of the occluding member 20a may be adjusted by connecting a first control wire 134 (FIG. 9B) to the first attachment mechanism 130 and then manipulating the first control wire in a clockwise or counter-clockwise manner. By manipulating the first tensioning mechanism 132, the length of the first control wire 134 may be increased or decreased to fine-tune the vertical tension of the occluding member 20a.

The second control wire 122 (FIG. 9A) may also comprise a proximal end portion 136 and a distal end portion 138. The distal end portion 138 may be operatively connected to the occluding member 20a at a second connecting point 140. As shown in FIG. 9A, for example, the distal end portion 138 of the second control wire 122 may be connected to a girth wire 142 circumferentially located about the occluding member 20a. The proximal end portion 136 of the second control wire 122 may comprise a second attachment mechanism 144 (FIG. 9B) fluidly connected to a second tensioning mechanism 146 (FIG. 9B). The second tensioning mechanism 146 can include a screw, for example, and may be manipulated so as to adjust or fine-tune the lateral tension of the occluding member 20a. For example, the lateral tension of the occluding member 20a may be adjusted by connecting a second control wire 148 (FIG. 9B) to the second attachment mechanism 144 and then manipulating the second control wire in a clockwise or counter-clockwise manner. By manipulating the second tensioning mechanism 146, the circumference of the girth wire 142 may be increased or decreased to fine-tune the lateral tension of the occluding member 20a.

The proximal end portion 14a of the apparatus 10a may be adapted for attachment to a detachable catheter 150. The detachable catheter 150 may be used to guide the apparatus 10a through a patient's vasculature, for example. As shown in FIGS. 9A and 9B, the proximal end portion 14a may include a release mechanism 152 for selectively releasing the apparatus 10a from the detachable catheter 150. The release mechanism 152 may comprise a plurality of screws integrally located at the proximal end portion 14a of the apparatus 10a, and corresponding receptacles (not shown) for the screws located about the detachable catheter 150.

At least one stopper 154 may be operatively located about the proximal end portion 14a of the apparatus 10a. The stopper 154 may comprise a plurality of post members 156 oppositely disposed about the proximal end portion 14a as shown in FIG. 9B. Alternatively, the stopper 154 may have a donut- or washer-like shape and may be circumferentially located about the proximal end portion 14a of the apparatus 10a. The stopper 154 may be used to secure the apparatus 10a in the left atrium 36, for example. Where the apparatus 10a is placed in the left atrium 36, the stopper 154 may be located in the right atrium 34 and abut the interatrial septum 42 so that the apparatus is secured in a desired position. Alternatively or additionally, the stopper 154 may be used to adjust the position of the apparatus 10a. Where the apparatus 10a is positioned in the left atrium 36, for example, the stopper 154 may be positioned more distally about the proximal end portion 14a so that the occluding member 20a is positioned more proximate to the mitral valve 52. Alternatively, the stopper 154 may be positioned more proximately about the proximal end portion 14a so that the occluding member 20a is positioned more distal to the mitral valve 52.

To facilitate positioning of the apparatus 10 in the mitral valve 52, the apparatus may include at least one radiographically opaque marking (not shown). The radiographically opaque marking may be located at the occluding member 20 or, alternatively, at any other portion of the suspending wire 12. The radiographically opaque marking can be any one or combination of materials or devices with significant opacity. Examples of such radiographically opaque markings include, but are not limited to, a steel mandrel sufficiently thick to be visible on fluoroscopy, a tantalumipolyurethane tip, a gold-plated tip, bands of platinum, stainless steel or gold, soldered spots of gold, and polymeric materials with a radiographically opaque filter such as barium sulfate.

Figure 10:
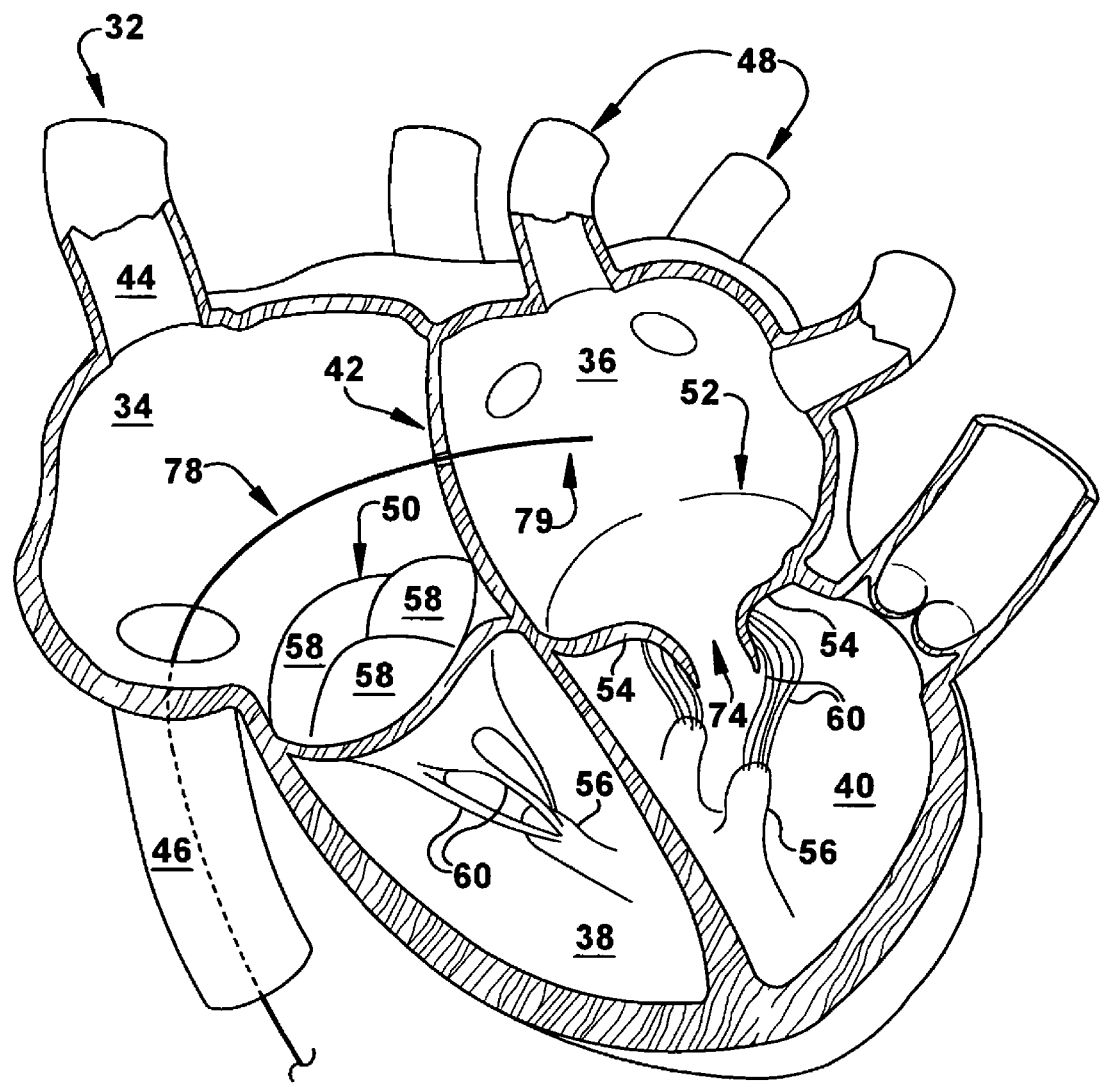
FIG. 10 is a cross-sectional view showing a guidewire extending trans-septally through the human heart.
Figure 11:
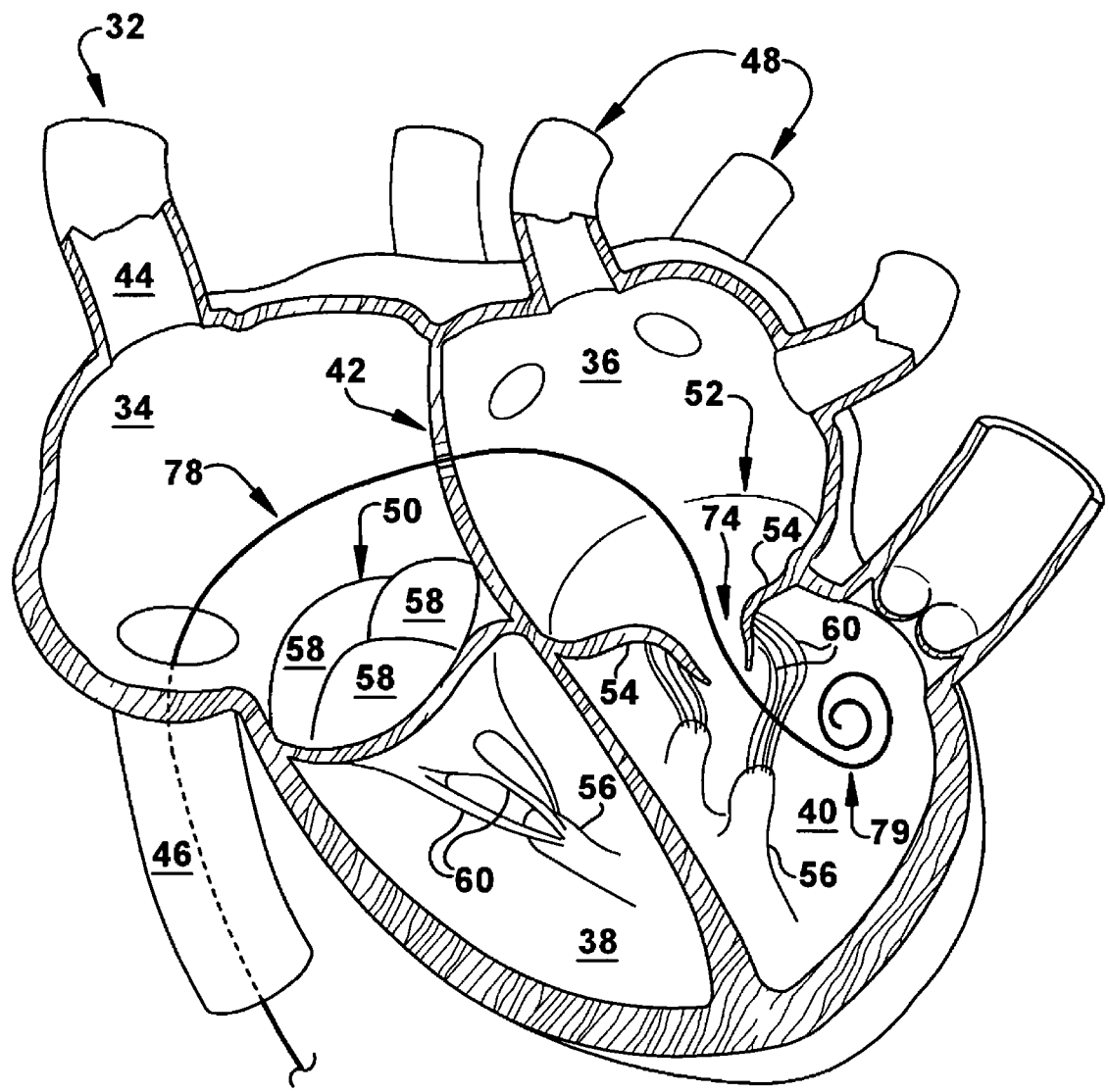
FIG. 11 is a cross-sectional view showing the guidewire extending through the mitral valve into the left ventricle.

To treat regurgitation of blood through a diseased heart valve 30, such as the mitral valve 52, the present invention may be delivered to the left atrium 36 as illustrated in FIGS. 10-16. A guidewire 78 is inserted into a patient's body via a femoral vein (not shown), jugular vein (not shown), another portion of the patient's vasculature, or directly into the body through a chest incision. Under image guidance (e.g., fluoroscopy, ultrasound, magnetic resonance, computed tomography, or combinations thereof), the guidewire 78 may be respectively steered through the patient's vasculature into the inferior vena cava 46 or superior vena cava 44 or through a chest incision and an apical puncture, as shall be discussed below. The guidewire 78 is then passed across the right atrium 34 so that the distal end 79 of the guidewire pierces the interatrial septum 42 as shown in FIG. 10. The guidewire 78 is extended across the left atrium 36 and then downward through the mitral valve 52 so that the distal end 79 of the guidewire is securely positioned in the left ventricle 40 (FIG. 11).

Figure 12:
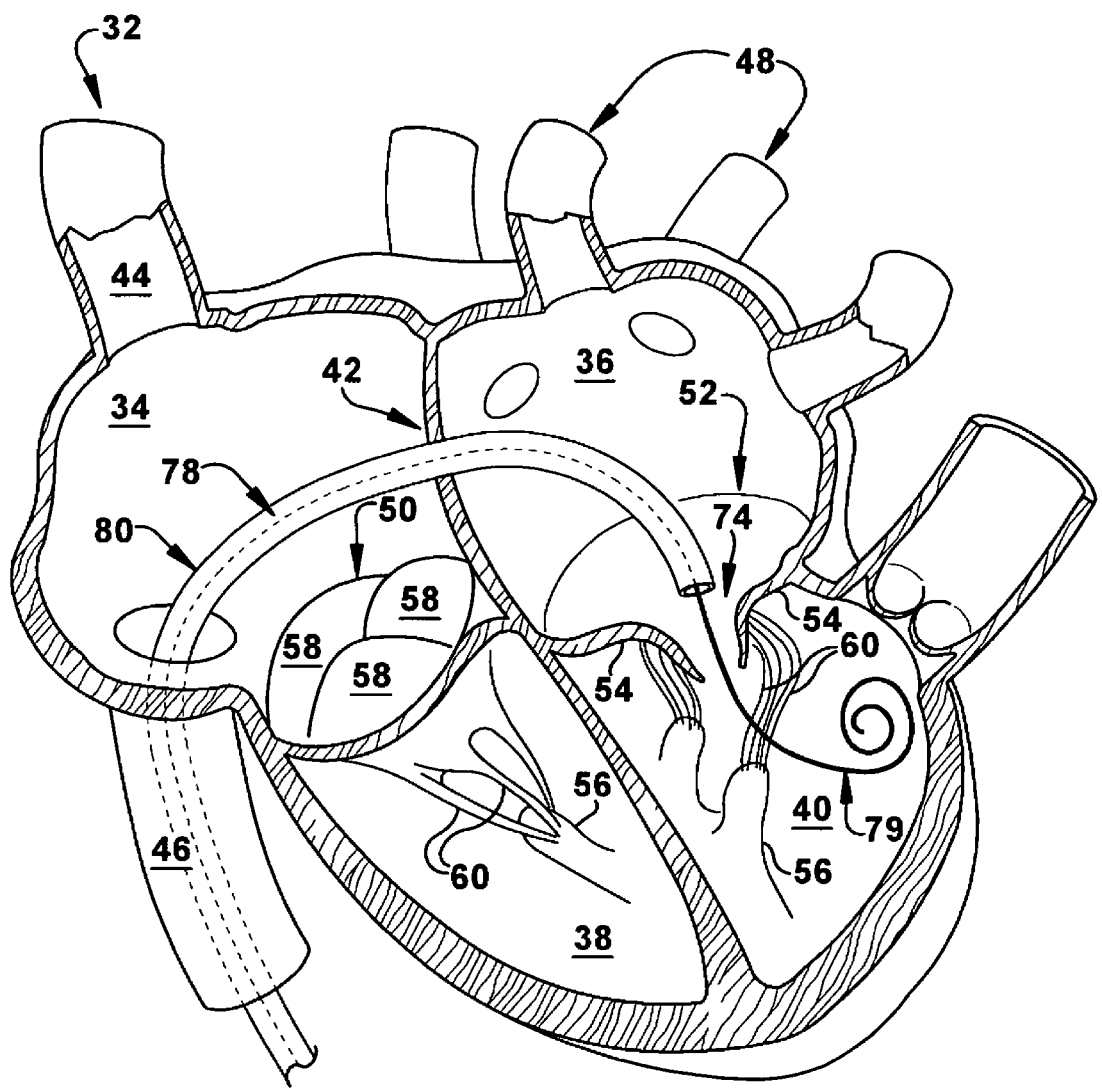
FIG. 12 is a cross-sectional view showing a catheter advanced over the guidewire.

After the guidewire 78 is appropriately positioned in the patient's heart 32, a catheter 80 is passed over the guidewire as shown in FIG. 12. The catheter 80 may be comprised of a flexible, resiliently yieldable material such as silicone, PTFE, ePTFE, plastic polymer, or the like.

Figure 13:
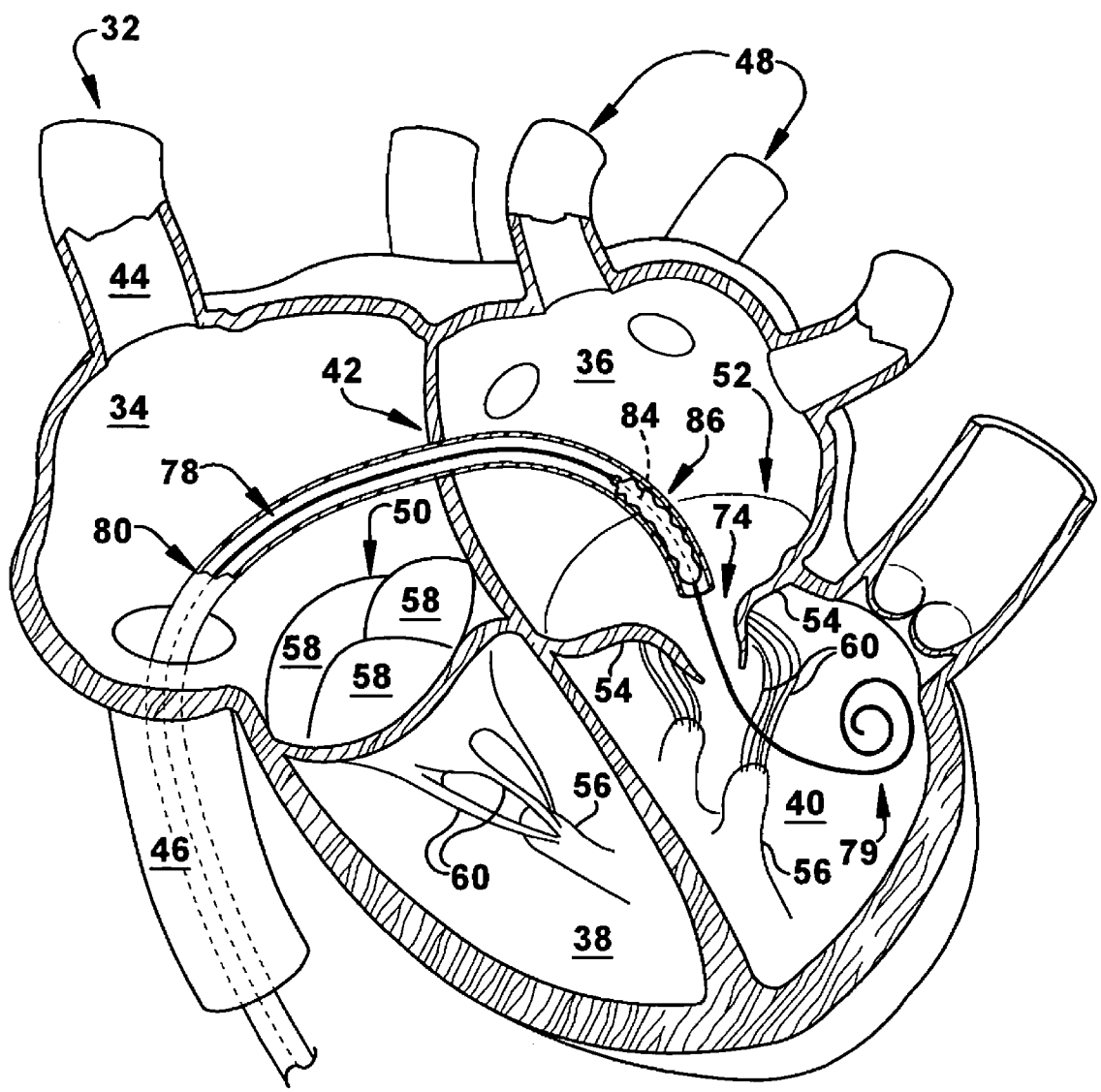
FIG. 13 is a cross-sectional view showing a deflated, two-layer balloon positioned within a distal end portion of the catheter.
Figure 14A:
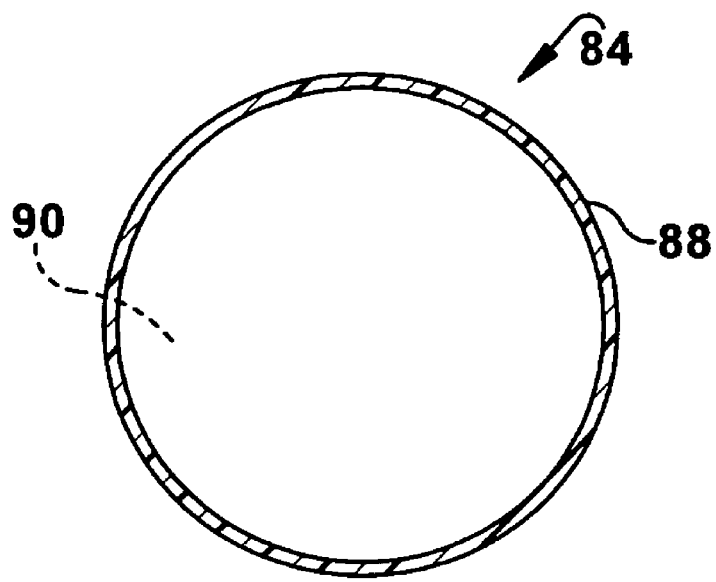
FIG. 14A is a cross-sectional view of the two-layer inflatable balloon in an inflated configuration.
Figure 14B:
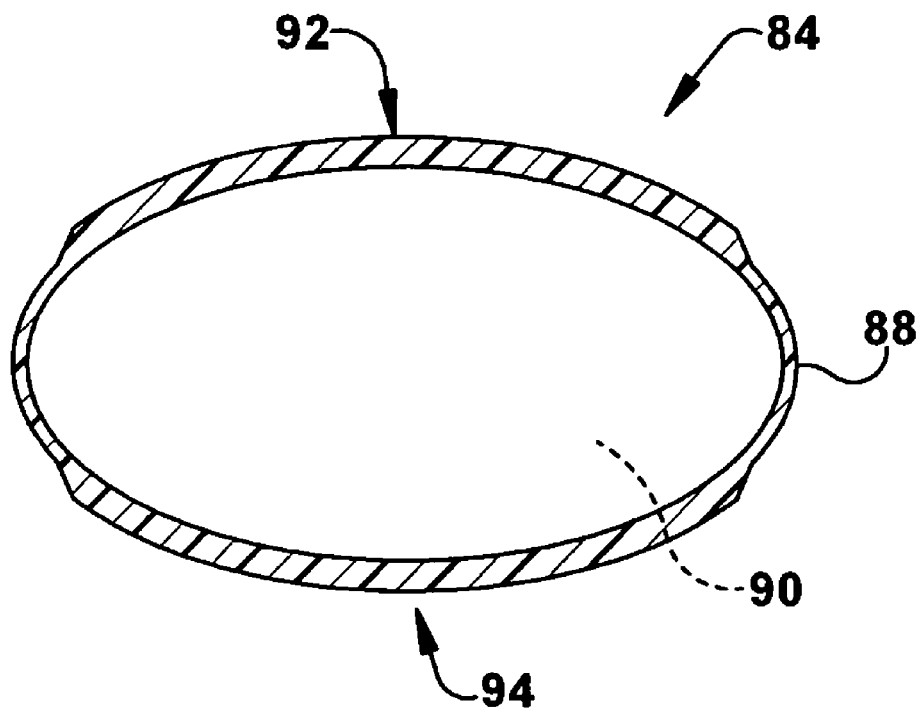
FIG. 14B is a cross-sectional view of the balloon shown in FIG. 14A in an ellipsoidal configuration.

An inflatable balloon 84 is next attached at the proximal end (not shown) of the guidewire 78 in a deflated configuration, and then advanced over the guidewire until the balloon is positioned within the distal end portion 86 of the catheter 80 (FIG. 13). The balloon 84 is used to measure the geometry of the regurgitant mitral valve orifice 74 and, as shown in FIG. 14A, has a two-layer configuration. The first layer 88 can be made from a conventional material, such as PTFE, elastomeric materials including latex, silicone, polyolefin copolymers, or any other suitable balloon materials known in the art. The second layer 90 may be made of a woven or braided cloth such as nylon, silk, gauze, ePTFE, or the like. The second layer 90 may have a uniform thickness and may fully or partially encapsulate the first layer 88. Alternatively, the second layer 90 may have different sections of varying thickness. As shown in FIG. 14B, for example, the anterior and posterior sections 92 and 94 of the second layer 90 may be thicker than other sections of the second layer. As a consequence, the thicker sections 92 and 94 impart a greater resistance to the first layer 88 when the balloon 84 is inflated and, as illustrated in FIG. 14B, cause the balloon to obtain an ellipsoidal or crescent-like shape.

Figure 15:
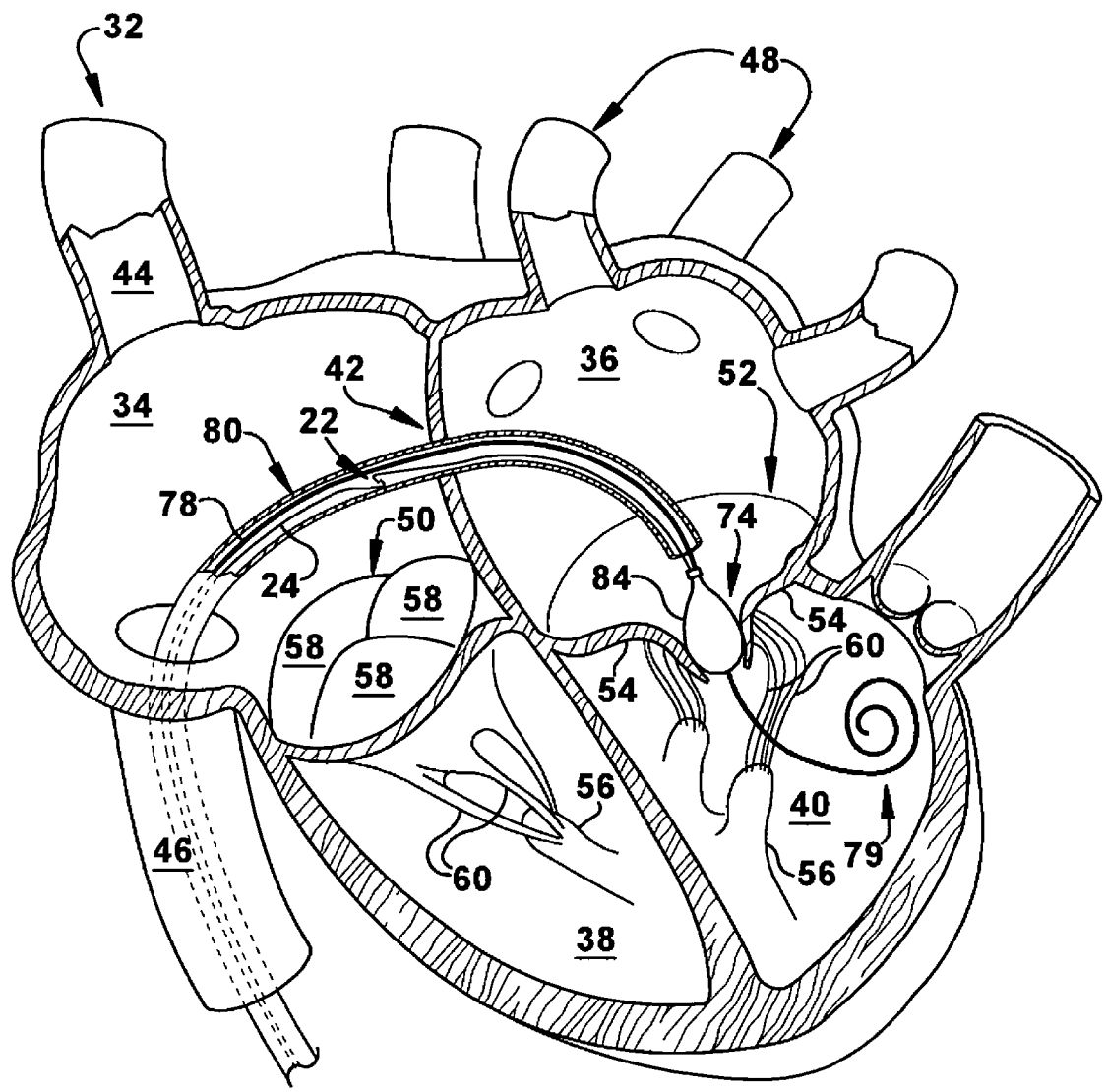
FIG. 15 is a cross-sectional view showing the balloon of FIG. 13 in an inflated configuration positioned between the leaflets of the mitral valve.

Once the balloon 84, in a deflated configuration, is positioned within the distal end portion 86 of the catheter 80, the catheter is then manipulated so that the balloon is progressively freed from the catheter. As shown in FIG. 15, the balloon 84 is then positioned in the regurgitant mitral valve orifice 74 and inflated so that at least one leaflet 54 of the mitral valve 52 coapts with at least one surface of the balloon. Coaptation of the valve leaflets 54 may be monitored by any image-based means. Where the balloon 84 has opacity, for example, magnetic resonance imagining (MRI) or computed tomography (CT) may be used to monitor the extent of coaptation between the leaflets 54 and the balloon.

Additionally, the amount of regurgitation through the mitral valve 52 may be monitored via an echocardiographic technique (e.g., transesophageal echocardiography, doppler echocardiography, 2-D echocardiography, and/or color echocardiography). When regurgitation has been sufficiently or entirely prevented, the geometry of the balloon 84 is then measured by, for example, determining the diameter of the balloon in a plurality of dimensions. Additionally, the length of the suspending wire 12 between the balloon 84 and the interatrial septum 42 may be measured by MRI, CT, ultrasound, fluoroscopy, or other similar technique.

After determining the geometry of the balloon 84, the balloon is deflated and removed from the patient's vasculature. Based upon the previously measured dimensions of the balloon 84, an appropriately-sized apparatus 10 is then selected. For instance, the selected apparatus 10 will have an occluding member 20 whose geometry corresponds to the measured geometry of the balloon 84. Additionally, where the length of the suspending wire 12 between the balloon 84 and the interatrial septum 42 was measured, the suspending wire of the apparatus 10 will also have the corresponding length.

Once the appropriately-sized apparatus 10 is selected, the apparatus is then attached to the proximal end (not shown) of the guidewire 78. A positioning wire 24 or other similar device useful for advancing the apparatus 10 over the guidewire is then attached to the connecting means 22 of the suspending wire 12. An axial force is applied to the positioning wire 24 so that the apparatus 10 is passed over the guidewire 78 and positioned at the distal end portion 86 of the catheter 80.

Figure 16:
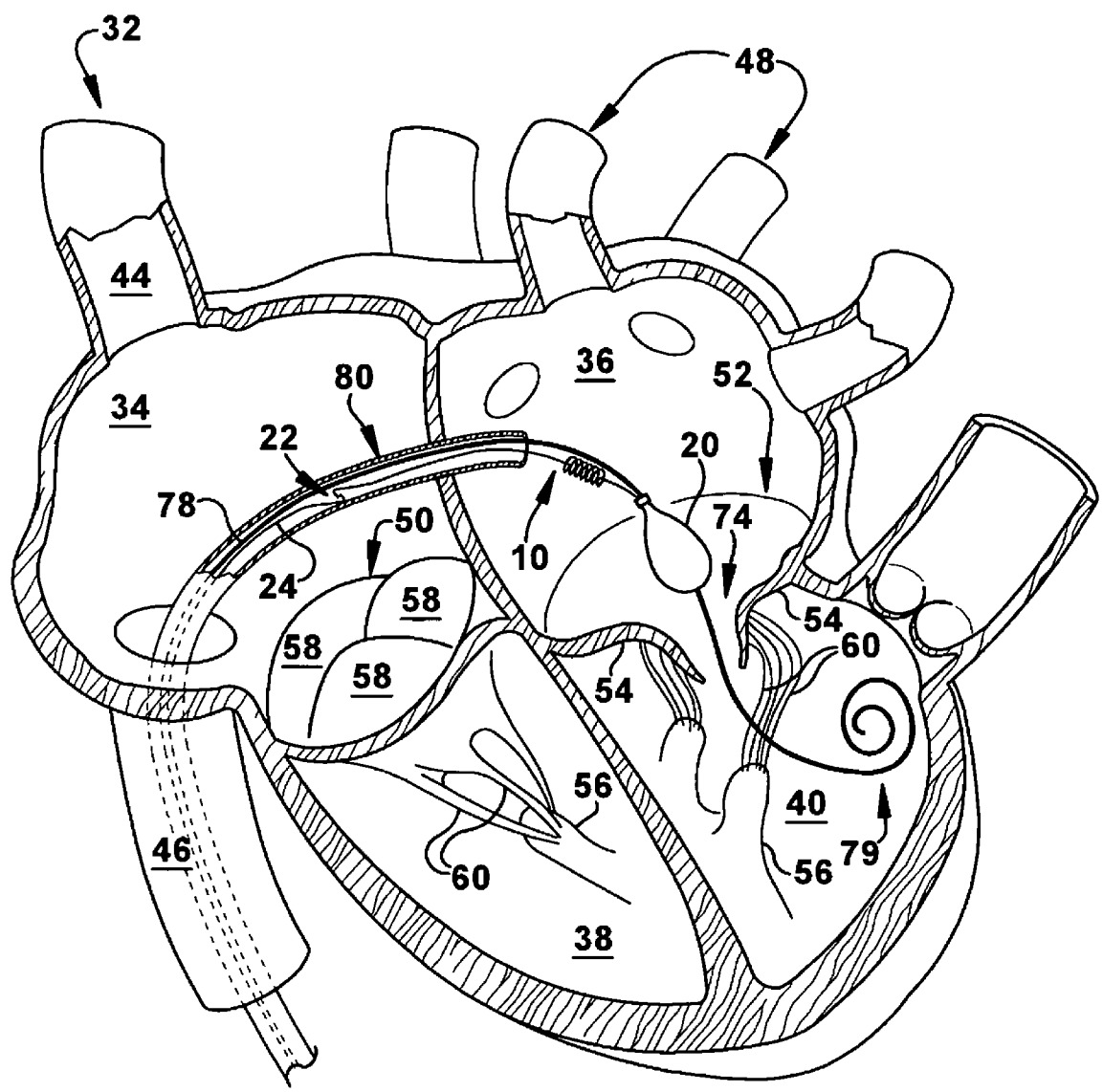
FIG. 16 is a cross-sectional view showing the apparatus of FIG. 1 partly deployed in the left atrium.

Upon reaching the distal end portion 86 of the catheter 80, the apparatus 10 is progressively freed from the catheter as shown in FIG. 16. As the apparatus 10 is progressively freed from the catheter 80, the position of the apparatus in the left atrium 36 can be monitored, controlled, and/or quality assured by imaging systems of various kinds. For example, X-ray machines, fluoroscopic machines, ultrasound, CT, MRI, positron emission tomography (PET), and other imaging devices may be used.

The apparatus 10 is next appropriately positioned in the left atrium 36 after being freed from the catheter 80. More specifically, the anchoring portion 26 is urged toward the interatrial septum 42 until the anchoring portion contacts the interatrial septum. The anchoring portion 26 is then manipulated so that the interatrial septum 42 is straddled by, or positioned between, at least two loop members 28. By straddling or positioning the interatrial septum 42 between loop members 28, the apparatus 10 is securely fixed in the left atrium 36.

Alternatively, where the anchoring portion 26 comprises a septal occluder 106, the anchoring portion may first be manipulated so that the septal occluder, in a collapsed configuration, is positioned approximately perpendicular to the interatrial septum 42. Then, the catheter 80 may be slowly retracted so that the flexible discs 108 of the septal occluder 106 may self-expand. As each of the flexible discs 108 expand, the interatrial septum 42 is securely straddled or braced between the flexible discs and the apparatus 10 is securely positioned in the left atrium 36.

After the anchoring portion 26 is secured, the position of the apparatus 10 may be adjusted so that the occluding member 20 is appropriately positioned in the regurgitant mitral valve orifice 74. For example, the anchoring portion 26 may be rotated in a clockwise or counter-clockwise manner so that the loop members 28 are carefully threaded and advanced across the interatrial septum 42. By threading the loop members 28 through the interatrial septum 42, the length of the suspending wire 12 and the position of the occluding member 20 may be adjusted as needed. Alternatively, the position of the occluding member 20 may be adjusted by cinching or bending the suspending wire 12.

Once the apparatus 10 is appropriately positioned in the left atrium 36, a stopper 100 or other similar device may be used to securely position the anchoring portion 26 (FIG. 17) in the interatrial septum 42. The stopper 100 may be urged along the positioning wire 24 and threaded over the anchoring portion 26 until the stopper is snugly positioned adjacent the interatrial septum 42. The stopper 100 may be made of rubber, for example, or any other similar material. By positioning the stopper 100 snugly against the interatrial septum 42, unwanted movement or flexion of the anchoring portion 26 is substantially hindered or prevented.

Figure 17:
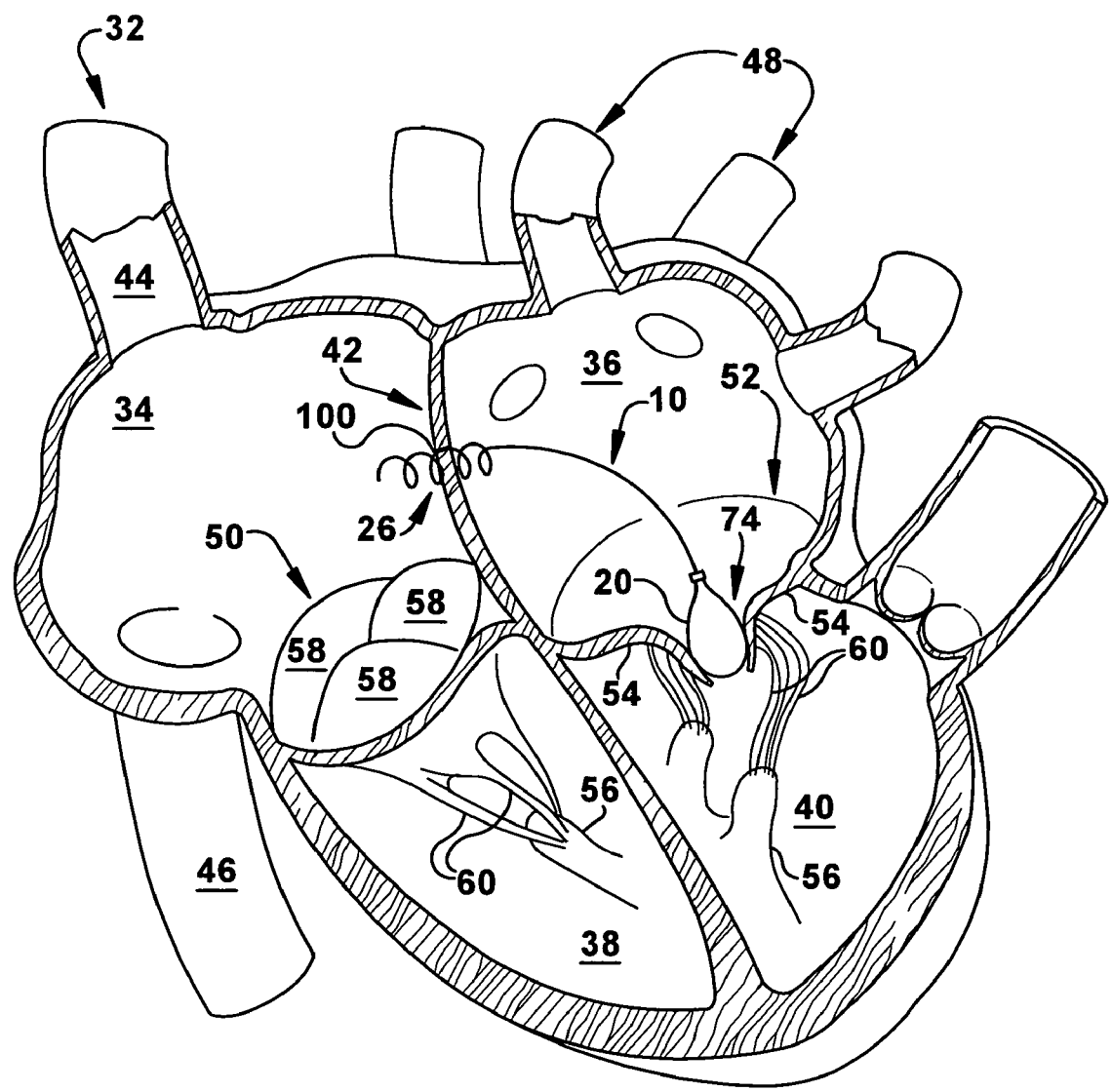
FIG. 17 is a cross-sectional view of the apparatus of FIG. 1 deployed in the left atrium.

Depending upon the location and geometry of the regurgitant mitral valve orifice 74, the occluding member 20 may be suspended at any one of a number of different positions. As illustrated in FIG. 17, for example, the occluding member 20 may be positioned approximately level to the annulus 70 of the mitral valve 52. Alternatively, at least a portion of the occluding member 20 may be positioned below the free ends of the mitral valve leaflets 54.

After the apparatus 10 is appropriately positioned in the left atrium 36, the positioning wire 24 is disconnected at the connecting mechanism 22 at the proximal end portion 14 of the apparatus and, along with the guidewire 78, withdrawn from the patient's body. With the occluding member 20 appropriately positioned in the mitral valve 52, at least one leaflet 54 of the mitral valve can coapt with the surface of the occluding member. In doing so, the leaflets 54 abut the occluding member 20 and buttress the mitral valve 52 so regurgitant blood flow is substantially reduced or eliminated during systole.

Figure 23:
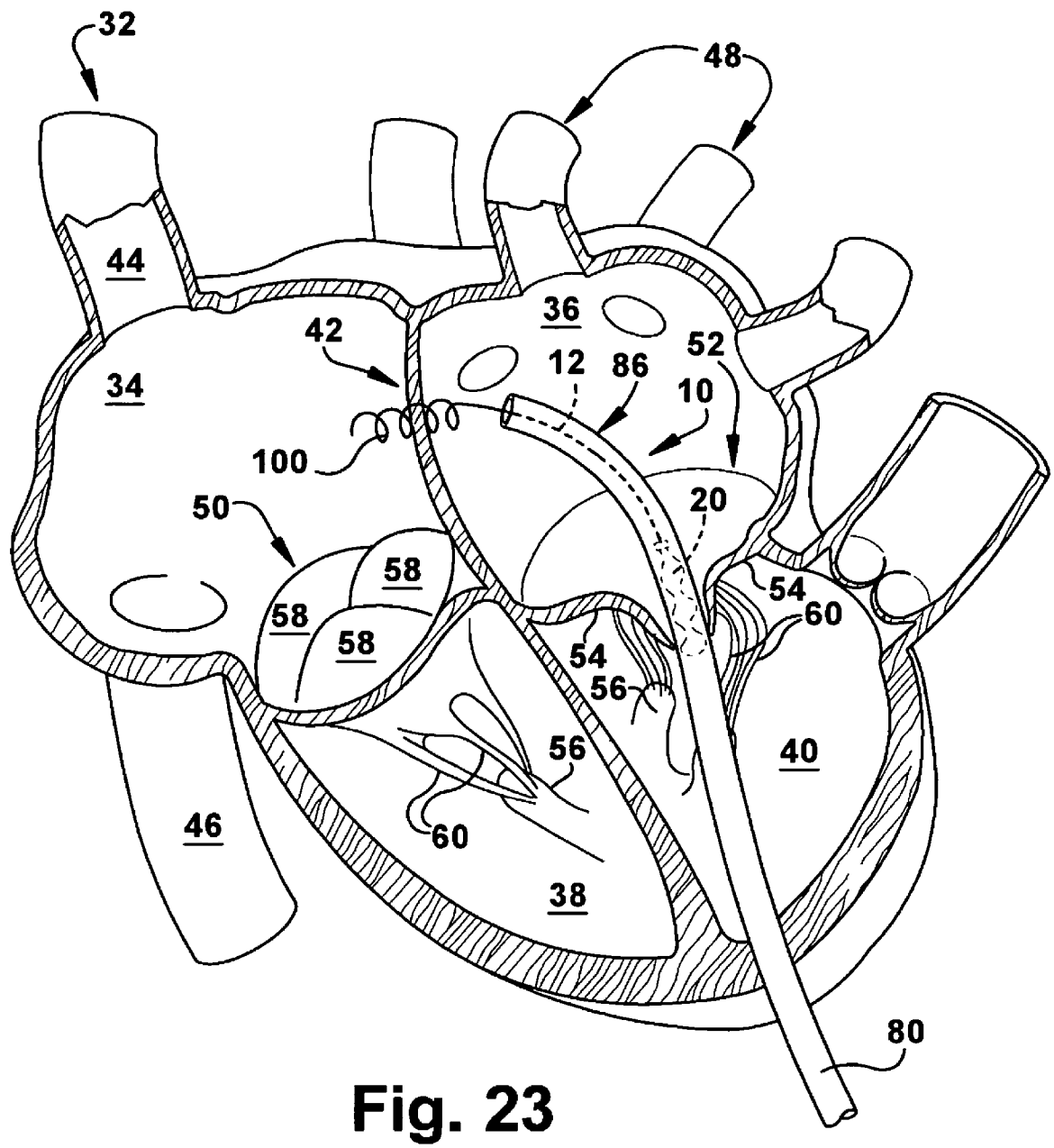
FIG. 23 is a cross-sectional view of the apparatus of FIG. 1 deployed in the left atrium.
Figure 24:
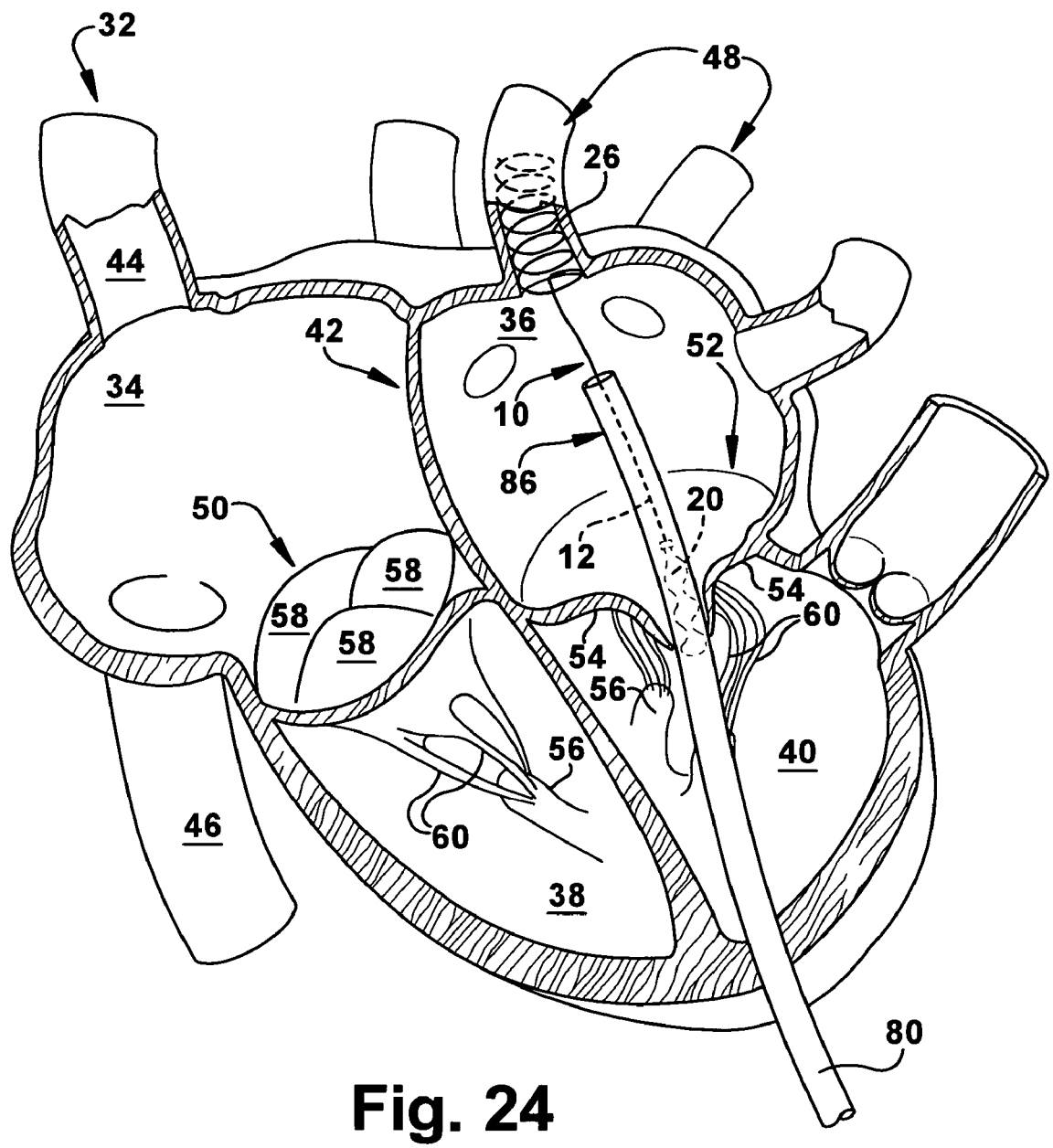
FIG. 24 is a cross-sectional view of the apparatus of FIG. 1 deployed in the left atrium.

A similar technique is used when the apparatus 10 is introduced into the patient's body non-percutaneously, such as through a chest incision and trocar (not shown). In this alternate method of installation, an apical puncture may be made in the heart, as shown in FIGS. 23 and 24. The catheter 80 may be passed through the mitral valve 52 from the left ventricle 40 to the left atrium 36. The apparatus 10 would then be anchored within the left atrium 36, with the occluding member 20 suspended by a suspending wire 12.

A major difference between the technique shown in FIGS. 23 and 24 and that described earlier is that here the apparatus 10 is loaded into the catheter 80 with the anchoring portion 26 emerging first from the catheter 80, followed by the suspending wire 12 and then the occluding member 20. In the embodiments of FIGS. 23 and 24, the apparatus 10 is anchored to a heart structure and then remains in place as the catheter 80 is withdrawn to expose the apparatus 10 in an installed condition.

As shown in FIG. 23, the stopper 26 may engage the interatrial septum 42 from the left atrium 36. When the stopper 100 is of the spiral anchoring member 100 type shown, the stopper may be screwed into the interatrial septum 42 by a rotating action of the positioning wire (omitted in this view for clarity). Alternately, a stopper 26 having flexible discs 108 connected by a connecting waist 110 may be used to affix the apparatus 10 to the interatrial septum 42 as described above with reference to FIGS. 8 and 8A.

As shown in FIG. 24, the anchoring portion 26 may instead engage a pulmonary vein 48 to suspend the apparatus 10 within the mitral valve 52. The anchoring portion 26 may be a spiral, springlike member (as shown in FIG. 24) adapted to exert a radially outward force to hold itself within the pulmonary vein 48. It is contemplated that a stent (not shown) could also or instead be used as an anchoring portion 26.

In an alternative embodiment of the present invention, the apparatus 10 may be used to reduce or eliminate regurgitant blood flow through a diseased tricuspid valve 50. The apparatus 10 shown in FIGS. 18-22 is identically constructed as the apparatus shown in FIG. 1, except as described below.

Figure 18:
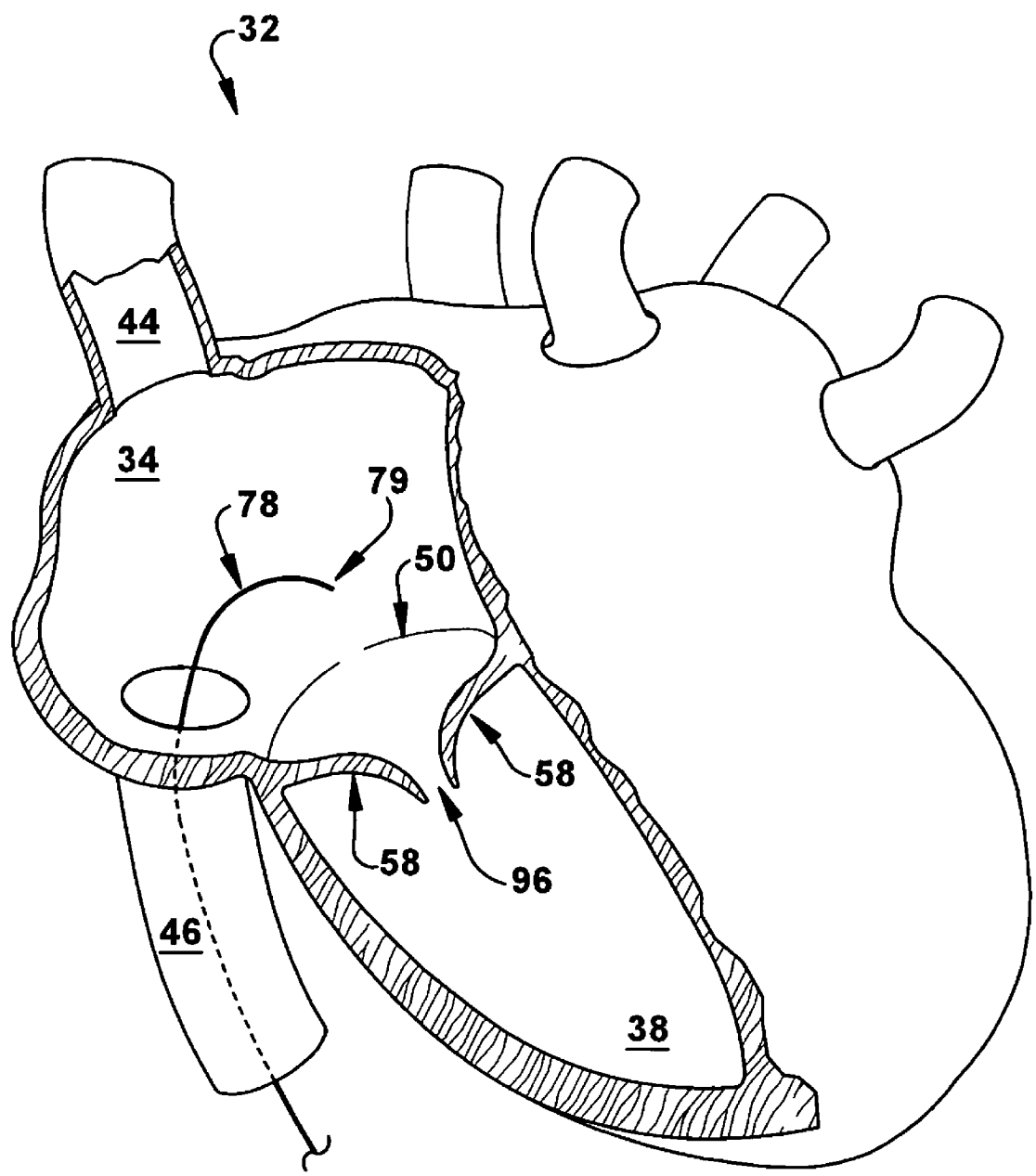
FIG. 18 is a cross-sectional view showing a guidewire extending through the inferior vena cava into the right atrium.

As shown in FIGS. 18-21, a percutaneous approach may be used to deliver the apparatus 10 to the diseased tricuspid valve 50. A guidewire 78 may be inserted into a patient's femoral vein (not shown) or jugular vein (not shown) and, under image guidance (e.g., fluoroscopy, ultrasound, magnetic resonance, computed tomography, or combinations thereof), respectively steered through the inferior vena cava 46 or superior vena cava 44 into the right atrium 34 (FIG. 18).

Figure 19:
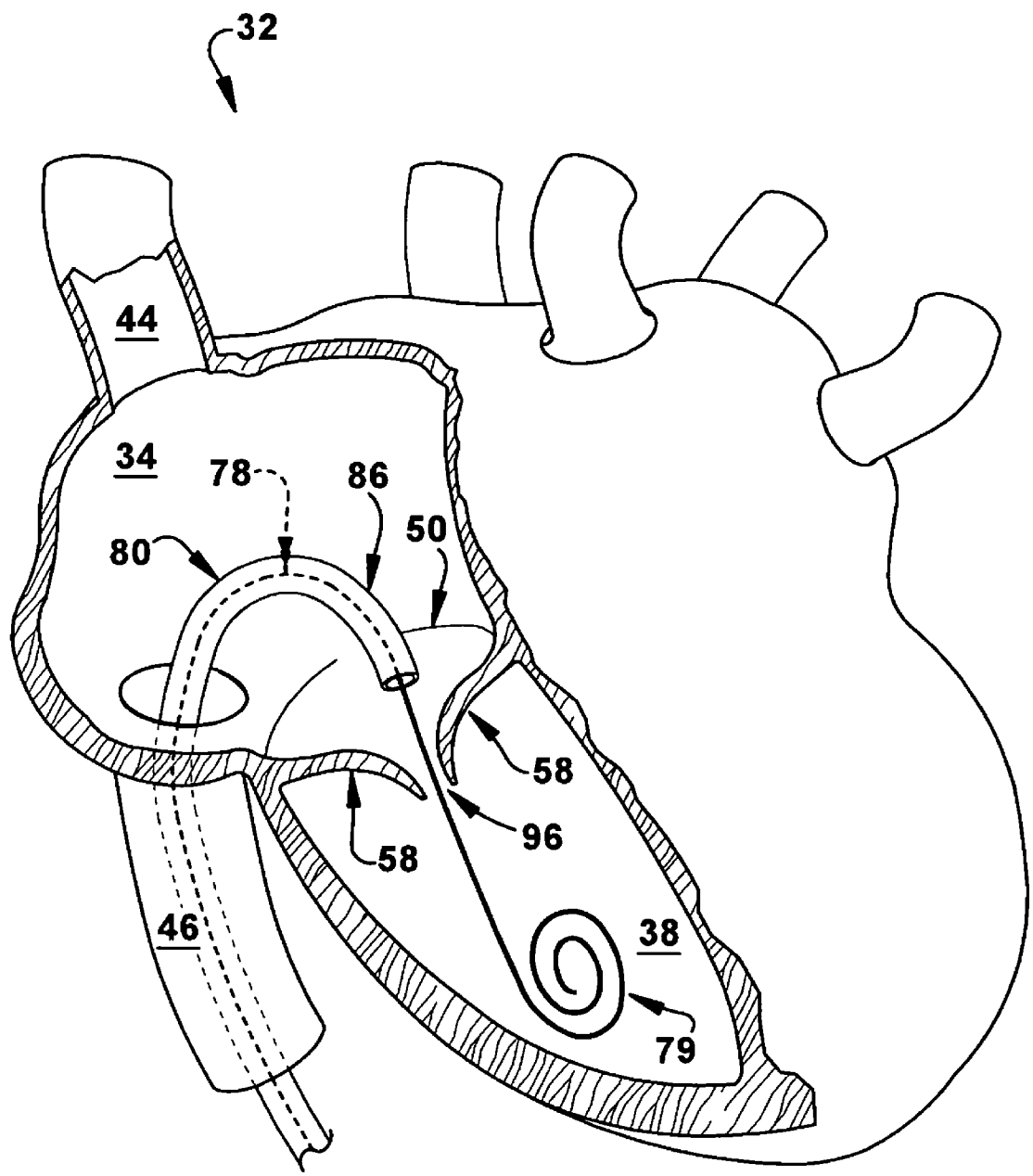
FIG. 19 is a cross-sectional view showing a catheter advanced over the guidewire.

Once the distal end 79 of the guidewire 78 has reached the right atrium 34, the distal end may be hinged downward toward the tricuspid valve 50. The guidewire 78 may then be urged through the tricuspid valve 50 so that the distal end 79 enters the right ventricle 38. The guidewire 78 may next be positioned in the right ventricle 38 so that the first guidewire is securely positioned within the inferior vena cava 46, the right atrium 34, and the right ventricle (FIG. 19).

After the guidewire 78 is secured in the patient's heart 32, a catheter 80 may be passed over the guidewire and advanced into the right atrium. The inflatable balloon 84 (FIG. 14A) may next be attached at the proximal end (not shown) of the guidewire 78 in a collapsed configuration, and then advanced over the guidewire until the balloon is positioned within the distal end portion 86 of the catheter 80. Once the balloon 84 is positioned at the distal end portion 86, the catheter 80 can be manipulated so that the balloon is progressively freed from the catheter. The balloon 84 may then be positioned in a regurgitant tricuspid valve orifice 96 and inflated so that at least one leaflet 58 of the tricuspid valve 50 coapts with at least one surface of the balloon. Coaptation of the valve leaflets 50 with the surface of the balloon 84 may be monitored by any image-based means. Where the balloon 84 has opacity, for example, MRI or CT may be used to monitor the degree of coaptation between the leaflets 58 and the balloon.

Additionally, the amount of regurgitation through the tricuspid valve 50 may be monitored via an echocardiographic technique (e.g., transesophageal echocardiography, doppler echocardiography, 2-D echocardiography, and/or color echocardiography). When regurgitation has been sufficiently or entirely prevented, the geometry of the balloon 84 may then be measured by, for example, determining the diameter of the balloon 84 in a plurality of dimensions. Additionally or optionally, the length of the suspending wire 12 between the balloon 84 and the inferior vena cava 46 may be measured by MRI, CT, ultrasound, fluoroscopy, or other similar technique.

After determining the geometry of the balloon 84, the balloon may be deflated and removed from the patient's vasculature. Based on the previously measured dimensions of the balloon 84, an appropriately-sized apparatus 10 may then be selected. For instance, the selected apparatus 10 may have an occluding member 20 whose geometry corresponds to the measured geometry of the balloon 84. Additionally, where the length of the suspending wire 12 between the balloon 84 and the inferior vena cava 46 was measured, the suspending wire of the apparatus 10 may have the corresponding length.

Once an appropriately-sized apparatus 10 is selected, the apparatus is then attached to the proximal end of the guidewire 78. A positioning wire 24 or other similar device useful for advancing the apparatus 10 over the guidewire 78 is operatively attached to the connecting means 22 of the suspending wire 12. An axial force is then applied to the positioning wire 24 so that the apparatus 10 is passed over the guidewire 78. The apparatus 10 is advanced along the guidewire 78 until the apparatus reaches the distal end portion 86 of the catheter 80.

Figure 20:
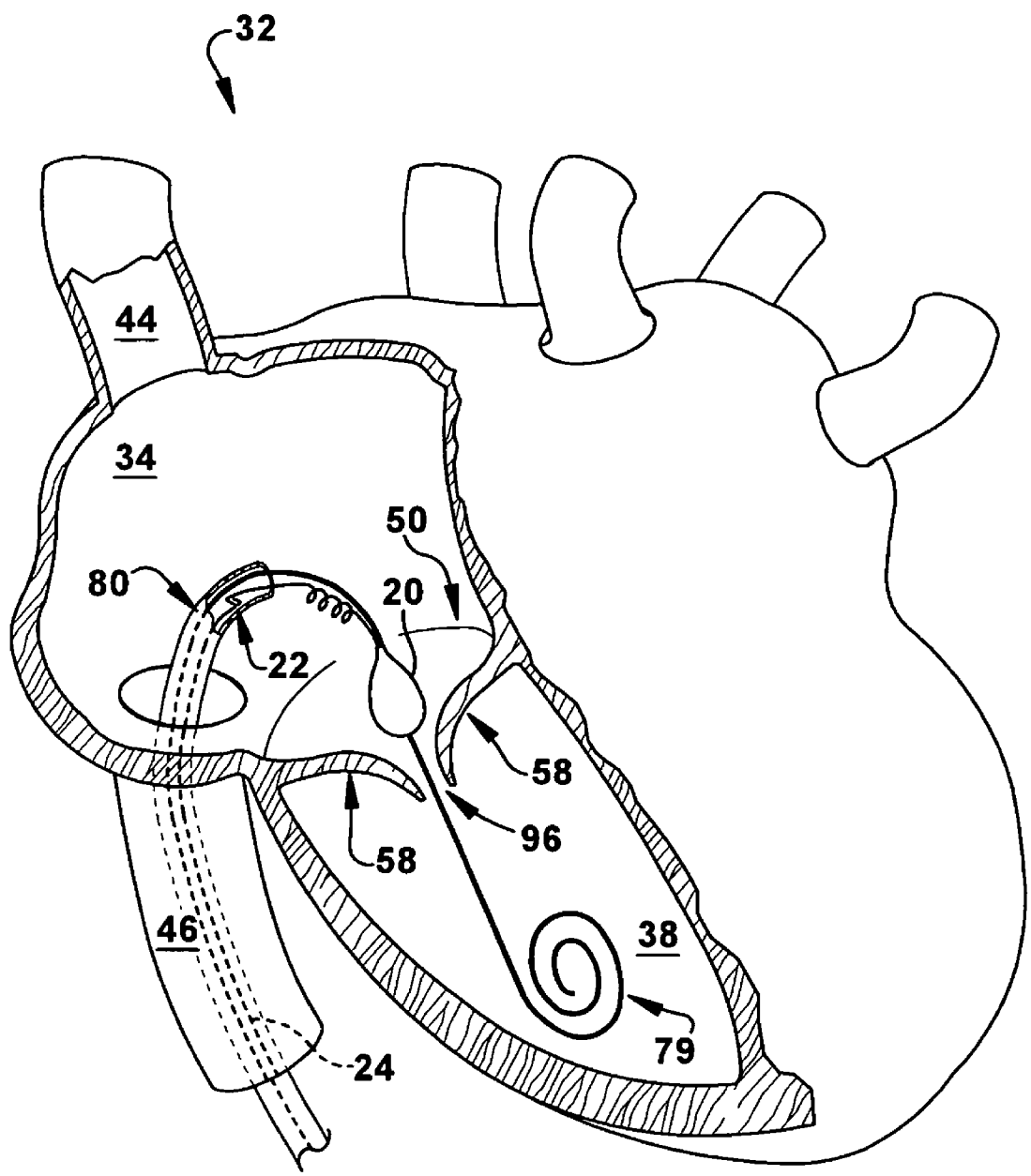
FIG. 20 is a cross-sectional view showing the apparatus of FIG. 1 partly deployed in the right atrium.

Upon reaching the distal end portion 86 of the catheter 80, the apparatus 10 is progressively freed from the catheter as shown in FIG. 20. As the apparatus 10 is progressively freed from the catheter 80, the position of the apparatus within the right atrium 34 can be monitored, controlled, and/or quality assured by imaging systems of various kinds. For example, X-ray machines, fluoroscopic machines, ultrasound, CT, MRI, PET, and other imaging devices may be used.

Figure 22:
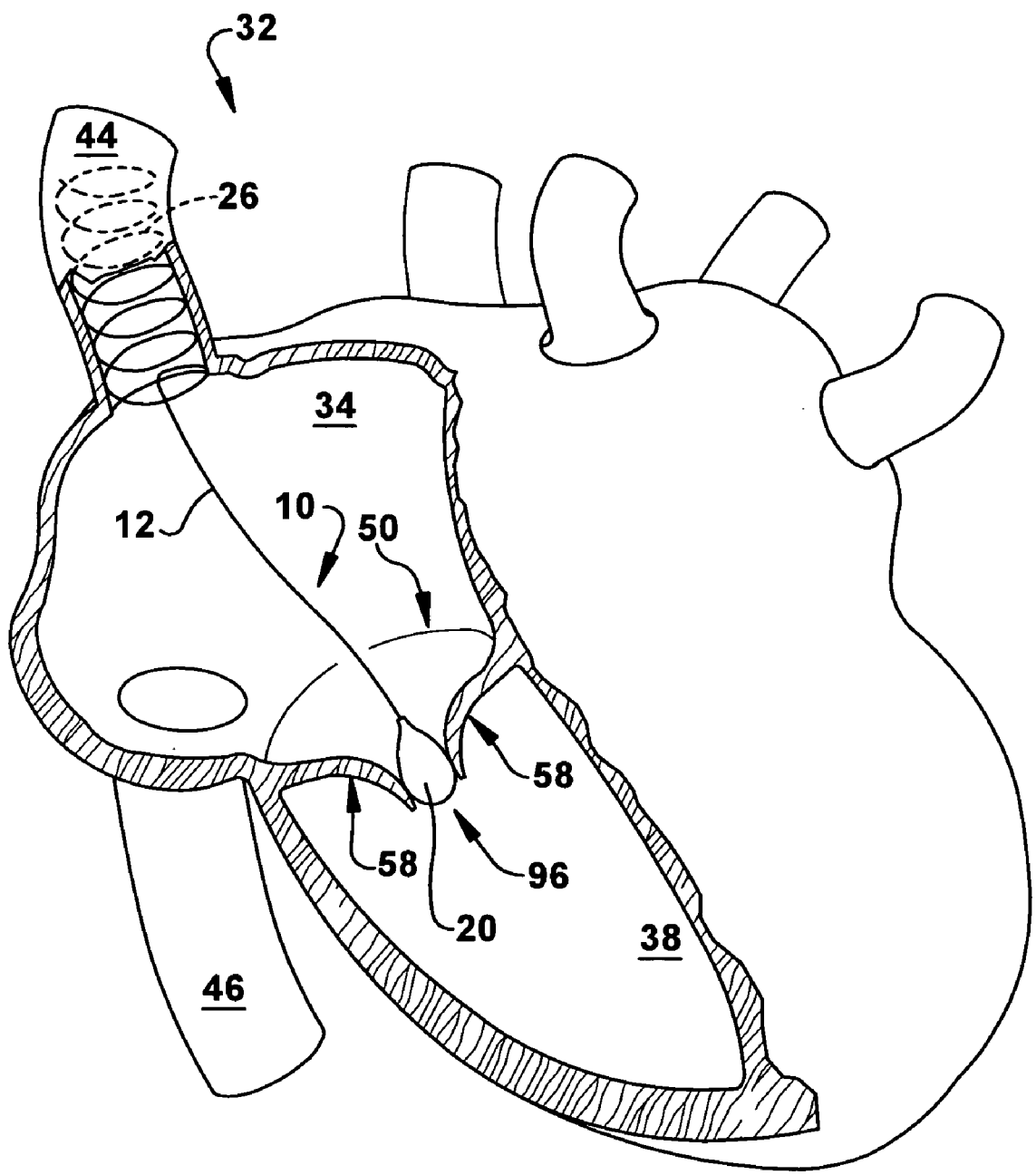
FIG. 22 is a cross-sectional view showing the apparatus of FIG. 1 deployed in the right atrium.

Once the apparatus 10 is freed from the catheter 80, the apparatus may be appropriately positioned in the right atrium 34. More particularly, the anchoring portion 26 may be urged toward the inferior vena cava 46 until at least one loop member 28 of the anchoring portion is disposed within the inferior vena cava. Placement of at least one loop member 28 in the inferior vena cava 46 serves to secure the anchoring portion 26 in the inferior vena cava as the coiled loop member(s) exert a resistance or pressure against the intraluminal surface of the inferior vena cava. The position of the occluding member 20 may be adjusted by rotating or twisting the anchoring portion 26 in a clock-wise or counter-clockwise manner so that the suspending wire 12 is advanced or retracted across the tricuspid valve 50. Alternatively, the position of the occluding member 20 may be adjusted by bending or cinching the suspending wire 12. It is contemplated that the anchoring portion 26 could alternatively be located in the superior vena cava 44, as shown in FIG. 22.

Figure 21:
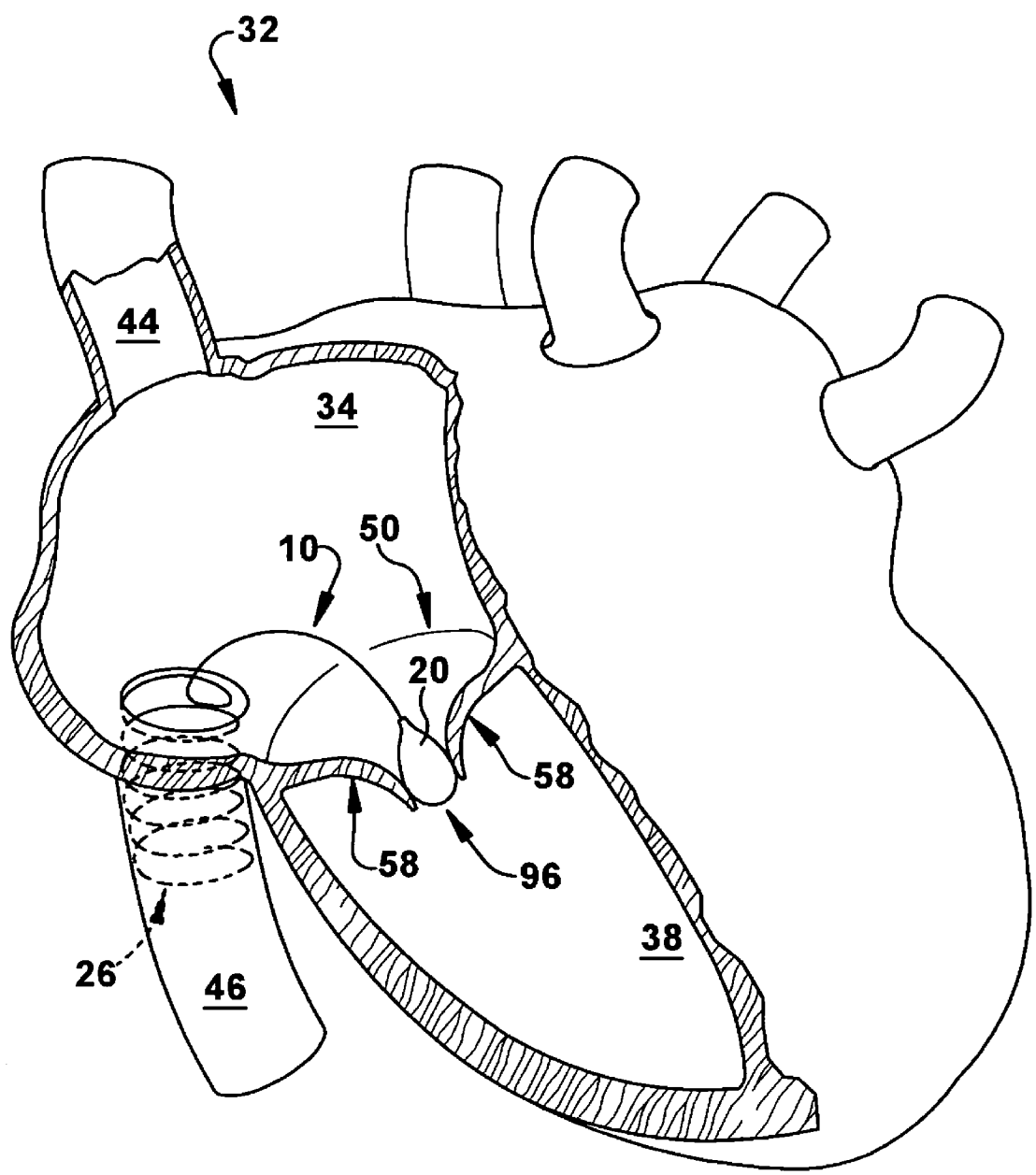
FIG. 21 is a cross-sectional view showing the apparatus of FIG. 1 deployed in the right atrium.

Depending upon the location and geometry of the regurgitant tricuspid valve orifice 96, the occluding member 20 may be suspended at any one of a number of different positions. As illustrated in FIG. 21, for example, the occluding member 20 may be positioned approximately level to the annulus 51 of the valve 50. Alternatively, the occluding member 20 may be positioned so that at least a portion of the occluding member is positioned below the free ends of the tricuspid valve leaflets 58.

After the apparatus 10 is appropriately positioned in the right atrium 34, the positioning wire 24 is disconnected from the proximal end portion 14 of the apparatus and, along with the guidewire 78, withdrawn from the patient's vasculature. With the occluding member 20 appropriately positioned in the regurgitant tricuspid valve orifice 96, at least one leaflet 58 of the tricuspid valve 50 can coapt with the surface of the occluding member. Consequently, the valve leaflets 58 abut the occluding member 20 and buttress the tricuspid valve 50 so that the regurgitant blood flow through the diseased tricuspid valve is substantially reduced or eliminated during systole.

The apparatus 10a shown in FIGS. 9A and 9B may also be used to hinder or prevent regurgitant blood flow through a diseased tricuspid valve 50 or mitral valve 52. The apparatus 10a may be delivered to the diseased tricuspid 50 or mitral valve 52 in a similar or identical manner as described above. Additionally, the apparatus 10a may be appropriately sized and subsequently secured in the left atrium 36 or right atrium 34 in a similar or identical manner as also described above. Once the apparatus 10a is appropriately positioned in the diseased tricuspid valve 50 or mitral valve 52, the geometry of the occluding member 20a may be fine-tuned as needed. For example, where an undesirable amount of regurgitant blood flow persists after placement of the apparatus 10a in the diseased tricuspid valve 50 or mitral valve 52, the lateral and/or vertical tension of the occluding member 20a may be adjusted so as to substantially reduce or eliminate the persistent regurgitant blood flow. More specifically, the first and second tensioning mechanisms 132 and 146 may be adjusted as needed in order to effectuate a desired change in the vertical and/or lateral dimensions (respectively) of the occluding member 20a.

From the above description of the invention, those skilled in the art will perceive improvements, changes and modifications. The apparatus 10 may be delivered to the heart 32 via a non-percutaneous method by, for example, obtaining open chest access to a diseased cardiac valve 30, as shown in the embodiment of FIGS. 23 and 24. Though the anchoring member 26 is shown in FIGS. 21, 22, and 24 as being a spiral or spring-like element, a stent (not shown) may be used also or instead in providing the anchoring function. Such improvements, changes and modifications within the skill of the art are intended to be covered by the appended claims.

Having described the invention, we claim:

1. An apparatus for treating regurgitation of blood through a diseased heart valve having at least two leaflets, said apparatus comprising:
   an occluding member configured to be positioned within the diseased heart valve so that at least a portion of said occluding member is positioned adjacent to one of the at least two leaflets of the heart valve, said portion contacting at least one surface of said at least one leaflet;
   said occluding member being dimensioned so that, during at least a portion of the cardiac cycle, said at least one leaflet abuts said at least one surface of said occluding member to mitigate regurgitation of blood through the heart valve;
   a suspending wire operatively attached to said occluding member and configured to facilitate positioning of said occluding member within the heart valve, said suspending wire including a proximal end portion and a distal end portion, the distance between said proximal and distal end portions comprising an intermediate portion; and
   said suspending wire comprising an anchoring portion, said anchoring portion comprising a septal occluder located at said intermediate portion of said suspending wire, said anchoring portion being configured to secure said suspending wire to an interatrial septum surrounding a heart chamber containing the heart valve;
   a safety wire operatively connected between said occluding member and said anchoring portion, said safety wire being coiled around said suspending wire; said safety wire being sufficiently flexible so as to not be subjected to the stress and strain of said suspending wire.

2. The apparatus of claim 1, wherein at least a portion of said occluding member is configured to be positioned between the valve leaflets.

3. The apparatus of claim 1, wherein at least a portion of said occluding member is configured to be positioned below the free ends of the valve leaflets.

4. The apparatus of claim 1, wherein at least a portion of said occluding member is configured to be positioned approximately at a level of the annulus of the valve.

5. The apparatus of claim 1, wherein said proximal end portion of said suspending wire includes a connecting mechanism for connecting said suspending wire to a positioning wire.

6. The apparatus claim 1, wherein said safety wire extends along said suspending wire and is independently attached thereto at a plurality of points.

7. The apparatus of claim 1, wherein said septal occluder comprises a plurality of oppositely opposed flexible discs, each of said flexible discs being fluidly connected by a connecting waist located intermediate said flexible discs.

8. The apparatus of claim 1, wherein said occluding member is completely covered by a membrane.

9. An apparatus for treating regurgitation of blood through a diseased heart valve having at least two leaflets, said apparatus comprising:
   an occluding member configured to be positioned within the diseased heart valve so that at least a portion of said occluding member is positioned adjacent to one of the at least two leaflets of the heart valve, said portion contacting at least one surface of said at least one leaflet;
   said occluding member being dimensioned so that, during at least a portion of the cardiac cycle, said at least one leaflet abuts said at least one surface of said occluding member to mitigate regurgitation of blood through the heart valve;
   a suspending wire operatively attached to said occluding member and configured to facilitate positioning of said occluding member within the heart valve, said suspending wire including a proximal end portion, and a distal end portion, said proximal end portion of said suspending wire including a connecting mechanism for connecting said suspending wire to a positioning wire, the distance between said proximal and distal end portions comprising an intermediate portion; and
   said suspending wire comprising an anchoring portion, said anchoring portion comprising a septal occluder located at said intermediate portion of said suspending wire, said anchoring portion being configured to secure said suspending wire to an interatrial septum surrounding a heart chamber containing the heart valve;
   a safety wire operatively connected between said occluding member and said anchoring portion, said safety wire being coiled around said suspending wire and being independently attached thereto at a plurality of points, said safety wire being sufficiently flexible so as to not be subjected to the stress and strain of said suspending wire.

10. An apparatus for treating regurgitation of blood through a diseased heart valve having at least two leaflets, said apparatus comprising:
    an occluding member configured to be positioned within the diseased heart valve so that at least a portion of said occluding member is positioned adjacent to one of the at least two leaflets of the heart valve, said portion contacting at least one surface of said at least one leaflet;
    said occluding member being dimensioned so that, during at least a portion of the cardiac cycle, said at least one leaflet abuts said at least one surface of said occluding member to mitigate regurgitation of blood through the heart valve;

a suspending wire operatively attached to said occluding member and configured to facilitate positioning of said occluding member within the heart valve, said suspending wire including a proximal end portion, and a distal end portion, said proximal end portion of said suspending wire including a connecting mechanism for connecting said suspending wire to a positioning wire, the distance between said proximal and distal end portions comprising an intermediate portion; and said suspending wire comprising an anchoring portion, said anchoring portion comprising a septal occluder located at said intermediate portion of said suspending wire, said anchoring portion being configured to secure said suspending wire to an interatrial septum surrounding a heart chamber containing the heart valve;

a safety wire operative connected between said occluding member and said anchoring portion, said safety wire being coiled around said suspending wire and being independently attached thereto at a plurality of points, said safety wire consisting of at least one thread made of a material selected from the group consisting of nylon, braided nylon, polytetrafluoroethylene (PTFE), expanded PTFE (ePTFE), and medical-grade sutures, said safety wire being sufficiently flexible so as to not be subjected to the stress and strain of said suspending wire.

* * * * *